(12) United States Patent
Seelen

(10) Patent No.: US 9,649,356 B2
(45) Date of Patent: May 16, 2017

(54) METHOD OF IMPROVING TRANSPLANT FUNCTION USING SOLUBLE COMPLEMENT RECEPTOR TYPE I (SCR1)

(75) Inventor: Marc Antonius Seelen, Rolde (NL)

(73) Assignee: CELLDEX THERAPEUTICS, INC., Needham, MA (US)

( * ) Notice: Subject to any disclaimer, the term of this patent is extended or adjusted under 35 U.S.C. 154(b) by 496 days.

(21) Appl. No.: 13/283,364

(22) Filed: Oct. 27, 2011

(65) Prior Publication Data
US 2012/0232020 A1  Sep. 13, 2012

Related U.S. Application Data

(60) Provisional application No. 61/407,331, filed on Oct. 27, 2010.

(51) Int. Cl.
A61K 38/17 (2006.01)
C07K 14/705 (2006.01)
A01N 1/02 (2006.01)

(52) U.S. Cl.
CPC .......... *A61K 38/177* (2013.01); *A01N 1/0226* (2013.01); *C07K 14/705* (2013.01)

(58) Field of Classification Search
CPC .................... C07K 14/472; A61K 38/1725
See application file for complete search history.

(56) References Cited

U.S. PATENT DOCUMENTS

| | | | |
|---|---|---|---|
| 5,252,216 A | 10/1993 | Folena-Wasserman et al. | |
| 5,456,909 A | 10/1995 | Marsh et al. | |
| 5,840,858 A | 11/1998 | Smith et al. | |
| 5,981,481 A | 11/1999 | Fearon et al. | |
| 6,169,068 B1 | 1/2001 | Levin et al. | |
| 6,193,979 B1 | 2/2001 | Rittershaus et al. | |
| 6,316,604 B1 | 11/2001 | Fearon et al. | |
| 6,458,360 B1 | 10/2002 | Fearon et al. | |
| 6,713,606 B1 | 3/2004 | Smith et al. | |

FOREIGN PATENT DOCUMENTS

| | | | |
|---|---|---|---|
| WO | 8909220 A1 | 10/1989 | |
| WO | WO 97/11601 | * 4/1997 | |

OTHER PUBLICATIONS

Naesens "Expression of Complement Components Differs Between Kidney Allografts from Living and Deceased Donors" J Am Soc Nephrol 20: 1839-1851, 2009, Epub May 14, 2009.*
Atkinson et al. "Complement-Dependent Inflammation and Injury in a Murine Model of Brain Dead Donor Hearts," Circ Res. 2009;105:1094-1101.*
Arumugam et al., "A small molecule C5a receptor antagonist protects kidneys from ischemia/reperfusion injury in rats", Kidney Int., 63(1): 134-142 (2003).
Damman et al., "Complement and renal transplantation: from donor to recipient", Transplantation, 85(7): 923-927 (2008).
Fearon, D.T., "Regulation of the amplification C3 convertase of human complement by an inhibitory protein isolated from human erythrocyte membrane", Proc. Natl. Acad. Sci. U.S.A., 76: 5867 (1979).
Fearon, D.T., "Identification of the membrane glycoprotein that is the C3b receptor of the human erythrocyte, polymorphonuclear leukocyte, B lymphocyte, and monocyte", J. Exp. Med., 152(1): 20 (1980).
Gottmann et al., "Atorvastatin donor pretreatment prevents ischemia/reperfusion injury in renal transplantation in rats: possible role for aldose-reductase inhibition", Transplantation, 84(6): 755-762 (2007).
Gottmann et al., "Influence of hypersulfated and low molecular weight heparins on ischemia/reperfusion: injury and allograft rejection in rat kidneys", Transpl. Int., 20(6): 542-549 (2007).
Gueler et al., "Complement 5a receptor inhibition improves renal allograft survival", J. Am. Soc. Nephrol., 19(12): 2302-2312 (2008).
Hoeger et al., "Modulation of brain dead induced inflammation by vagus nerve stimulation", Am. J. Transplant., 10(3): 477-489 (2010).
Kinoshita, T., "Biology of complement: the overture", Immunol. Today, 12(9): 291-295 (1991).
Kusaka et al., "Activation of inflammatory mediators in rat renal isografts by donor brain death", Transplantation, 69(3): 405-410 (2000).
Liu et al., "Donor dopamine pretreatment inhibits tubulitis in renal allografts subjected to prolonged cold preservation", Transplantation, 83(3): 297-303 (2007).
Matas et al., "Immunologic and nonimmunologic factors: different risks for cadaver and living donor transplantation", Transplantation, 69(1): 54-58 (2000).
Matthijsen, R.A., "Inhibition of complement factor C5 protects against renal ischemia-reperfusion injury: inhibition of late apoptosis and inflammation", Transplantation, 75(3): 375-382 (2003).
Nijboer et al., "Effect of brain death on gene expression and tissue activation in human donor kidneys", Transplantation, 78(7): 978-986 (2004).
Nussenzweig et al., "Complement receptor is an inhibitor of the complement cascade", J. Exp. Med., 153(5): 1138-1150 (1981).
Patel et al., "Therapeutic Strategy with a Membrane-Localizing Complement Regulator to Increase the Number of Usable Donor Organs after Prolonged Cold Storage", J. Am. Soc. Nephrol., 17: 1102-1111 (2006).
Pierre, Dissertation entitled "The Effect of Complement Inhibition with Soluble Complement Receptor 1 (SCR1) on Pig Allo-transplant Lung Function", The Institute of Medical Science, University of Toronto, (1997).
Pratt, J.R., "Allograft immune response with sCR1 intervention", Transpl. Immunol., 4(1): 72-75 (1996).

(Continued)

*Primary Examiner* — Christina Bradley
(74) *Attorney, Agent, or Firm* — Leon R. Yankwich; David G. O'Brien; Yankwich & Associates, P.C.

(57) ABSTRACT

A method is disclosed for inhibiting complement activation in brain-dead organ donors, particularly kidney donors, which leads to improvement of organ function of transplanted organs in recipients. The method involves administration of a complement inhibitory protein, specifically a soluble complement receptor type I (sCR1) polypeptide to the donor prior to harvesting the organ for transplant.

7 Claims, 3 Drawing Sheets

(56) References Cited

OTHER PUBLICATIONS

Pratt et al., "Local synthesis of complement component C3 regulates acute renal transplant rejection", Nat. Med., 8(6): 582-587 (2002).

Pruitt et al., "The effect of soluble complement receptor type 1 on hyperacute allograft rejection", J. Surg. Res., 50(4): 350 (1991).

Pruitt et al., "The effect of soluble complement receptor type 1 on hyperacute xenograft rejection", Transplantation, 52(5): 868 (1991).

Rittershaus et al., "Recombinant Glycoproteins That Inhibit Complement Activation and Also Bind the Selectin Adhesion Molecules", J. Biol. Chem., 274(16): 11237-11244 (1999).

Scesney et al., "A soluble deletion mutant of the human complement receptor type 1, which lacks the C4b binding site, is a selective inhibitor of the alternative complement pathway", Eur. J. Immunol., 26(8): 1729-1735 (1996).

Schuurs et al., "Distinct transcriptional changes in donor kidneys upon brain death induction in rats: insights in the processes of brain death", Am. J. Transplant, 4(12): 1972-1981 (2004).

Serinsoz et al., "Local complement C3 expression is upregulated in humoral and cellular rejection of renal allografts", Am. J. Transplant, 5(6): 1490-1494 (2005).

Solez et al., "International standardization of criteria for the histologic diagnosis of renal allograft rejection: the Banff working classification of kidney transplant pathology", Kidney Int., 44(2): 411-422 (1993).

Solez et al., "Banff 07 classification of renal allograft pathology: updates and future directions", Am. J. Transplant., 8: 753-760 (2008).

Terasaki et al., "High survival rates of kidney transplants from spousal and living unrelated donors", N. Engl. J. Med., 333(6): 333-336 (1995).

Walport et al., "Complement. First of two parts", N. Engl. J. Med., 344(14): 1058-1066 (2001).

Walport et al., "Complement. Second of two parts", N. Engl. J. Med., 344(15): 1140-1144 (2001).

Weisman et al., "Soluble human complement receptor type 1: in vivo inhibitor of complement suppressing post-ischemic myocardial inflammation and necrosis", Science, 249(4965): 146-151 (1990).

Yeh et al., "Recombinant soluble human complement receptor type 1 inhibits inflammation in the reversed passive arthus reaction in rats", J. Immunol., 146(1): 250 (1991).

Zheng et al., "Preventing renal ischemia-reperfusion injury using small interfering RNA by targeting complement 3 gene", Am. J. Transplant, 6(9): 2099-2108 (2006).

Zheng et al., "Gene silencing of complement C5a receptor using siRNA for preventing ischemia/reperfusion injury", Am. J. Pathol., 173(4): 973-980 (2008).

Zhou et al., "Predominant role for C5b-9 in renal ischemia/reperfusion injury", J. Clin. Invest., 105(10): 1363-1371 (2000).

Sacks et al., "The role of complement in the early immune response to transplantation", Nature Reviews, 12: 431-442 (2012).

Smith et al., "Review: Membrane-targeted complement inhibitors", Molecular Immunology, 38: 249-255 (2001).

\* cited by examiner (A)

(B)

SEQUENCE LISTING

<160> NUMBER OF SEQ ID NOS: 15

<210> SEQ ID NO 1
<211> LENGTH: 1931
<212> TYPE: PRT
<213> ORGANISM: Homo sapiens
<220> FEATURE:
<221> NAME/KEY: MISC_FEATURE
<222> LOCATION: (1)..(1931)
<223> OTHER INFORMATION: soluble CR1 polypeptide
<400> SEQUENCE: 1

```
Gln Cys Asn Ala Pro Glu Trp Leu Pro Phe Ala Arg Pro Thr Asn Leu
1               5                   10                  15

Thr Asp Glu Phe Glu Phe Pro Ile Gly Thr Tyr Leu Asn Tyr Glu Cys
            20                  25                  30

Arg Pro Gly Tyr Ser Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg
```

```
            50                  55                  60
Asn Pro Pro Asp Pro Val Asn Gly Met Val His Val Ile Lys Gly Ile
 65                  70                  75                  80

Gln Phe Gly Ser Gln Ile Lys Tyr Ser Cys Thr Lys Gly Tyr Arg Leu
                 85                  90                  95

Ile Gly Ser Ser Ser Ala Thr Cys Ile Ile Ser Gly Asp Thr Val Ile
                100                 105                 110

Trp Asp Asn Glu Thr Pro Ile Cys Asp Arg Ile Pro Cys Gly Leu Pro
                115                 120                 125

Pro Thr Ile Thr Asn Gly Asp Phe Ile Ser Thr Asn Arg Glu Asn Phe
                130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
                180                 185                 190

Ile Pro Asn Lys Cys Thr Pro Pro Asn Val Glu Asn Gly Ile Leu Val
                195                 200                 205

Ser Asp Asn Arg Ser Leu Phe Ser Leu Asn Glu Val Val Glu Phe Arg
                210                 215                 220

Cys Gln Pro Gly Phe Val Met Lys Gly Pro Arg Arg Val Lys Cys Gln
225                 230                 235                 240

Ala Leu Asn Lys Trp Glu Pro Glu Leu Pro Ser Cys Ser Arg Val Cys
                245                 250                 255

Gln Pro Pro Pro Asp Val Leu His Ala Glu Arg Thr Gln Arg Asp Lys
                260                 265                 270

Asp Asn Phe Ser Pro Gly Gln Glu Val Phe Tyr Ser Cys Glu Pro Gly
                275                 280                 285

Tyr Asp Leu Arg Gly Ala Ala Ser Met Arg Cys Thr Pro Gln Gly Asp
                290                 295                 300

Trp Ser Pro Ala Ala Pro Thr Cys Glu Val Lys Ser Cys Asp Asp Phe
305                 310                 315                 320

Met Gly Gln Leu Leu Asn Gly Arg Val Leu Phe Pro Val Asn Leu Gln
                325                 330                 335

Leu Gly Ala Lys Val Asp Phe Val Cys Asp Glu Gly Phe Gln Leu Lys
                340                 345                 350

Gly Ser Ser Ala Ser Tyr Cys Val Leu Ala Gly Met Glu Ser Leu Trp
                355                 360                 365

Asn Ser Ser Val Pro Val Cys Glu Gln Ile Phe Cys Pro Ser Pro Pro
                370                 375                 380

Val Ile Pro Asn Gly Arg His Thr Gly Lys Pro Leu Glu Val Phe Pro
385                 390                 395                 400

Phe Gly Lys Ala Val Asn Tyr Thr Cys Asp Pro His Pro Asp Arg Gly
                405                 410                 415

Thr Ser Phe Asp Leu Ile Gly Glu Ser Thr Ile Arg Cys Thr Ser Asp
                420                 425                 430

Pro Gln Gly Asn Gly Val Trp Ser Ser Pro Ala Pro Arg Cys Gly Ile
                435                 440                 445

Leu Gly His Cys Gln Ala Pro Asp His Phe Leu Phe Ala Lys Leu Lys
                450                 455                 460

Thr Gln Thr Asn Ala Ser Asp Phe Pro Ile Gly Thr Ser Leu Lys Tyr
465                 470                 475                 480
```

```
Glu Cys Arg Pro Glu Tyr Tyr Gly Arg Pro Phe Ser Ile Thr Cys Leu
            485                 490                 495

Asp Asn Leu Val Trp Ser Ser Pro Lys Asp Val Cys Lys Arg Lys Ser
            500                 505                 510

Cys Lys Thr Pro Pro Asp Pro Val Asn Gly Met Val His Val Ile Thr
            515                 520                 525

Asp Ile Gln Val Gly Ser Arg Ile Asn Tyr Ser Cys Thr Thr Gly His
            530                 535                 540

Arg Leu Ile Gly His Ser Ser Ala Glu Cys Ile Leu Ser Gly Asn Ala
545                 550                 555                 560

Ala His Trp Ser Thr Lys Pro Pro Ile Cys Gln Arg Ile Pro Cys Gly
            565                 570                 575

Leu Pro Pro Thr Ile Ala Asn Gly Asp Phe Ile Ser Thr Asn Arg Glu
            580                 585                 590

Asn Phe His Tyr Gly Ser Val Val Thr Tyr Arg Cys Asn Pro Gly Ser
            595                 600                 605

Gly Gly Arg Lys Val Phe Glu Leu Val Gly Glu Pro Ser Ile Tyr Cys
            610                 615                 620

Thr Ser Asn Asp Asp Gln Val Gly Ile Trp Ser Gly Pro Ala Pro Gln
625                 630                 635                 640

Cys Ile Ile Pro Asn Lys Cys Thr Pro Pro Asn Val Glu Asn Gly Ile
            645                 650                 655

Leu Val Ser Asp Asn Arg Ser Leu Phe Ser Leu Asn Glu Val Val Glu
            660                 665                 670

Phe Arg Cys Gln Pro Gly Phe Val Met Lys Gly Pro Arg Arg Val Lys
            675                 680                 685

Cys Gln Ala Leu Asn Lys Trp Glu Pro Glu Leu Pro Ser Cys Ser Arg
            690                 695                 700

Val Cys Gln Pro Pro Pro Asp Val Leu His Ala Glu Arg Thr Gln Arg
705                 710                 715                 720

Asp Lys Asp Asn Phe Ser Pro Gly Gln Glu Val Phe Tyr Ser Cys Glu
            725                 730                 735

Pro Gly Tyr Asp Leu Arg Gly Ala Ala Ser Met Arg Cys Thr Pro Gln
            740                 745                 750

Gly Asp Trp Ser Pro Ala Ala Pro Thr Cys Glu Val Lys Ser Cys Asp
            755                 760                 765

Asp Phe Met Gly Gln Leu Leu Asn Gly Arg Val Leu Phe Pro Val Asn
            770                 775                 780

Leu Gln Leu Gly Ala Lys Val Asp Phe Val Cys Asp Glu Gly Phe Gln
785                 790                 795                 800

Leu Lys Gly Ser Ser Ala Ser Tyr Cys Val Leu Ala Gly Met Glu Ser
            805                 810                 815

Leu Trp Asn Ser Ser Val Pro Val Cys Glu Gln Ile Phe Cys Pro Ser
            820                 825                 830

Pro Pro Val Ile Pro Asn Gly Arg His Thr Gly Lys Pro Leu Glu Val
            835                 840                 845

Phe Pro Phe Gly Lys Ala Val Asn Tyr Thr Cys Asp Pro His Pro Asp
            850                 855                 860

Arg Gly Thr Ser Phe Asp Leu Ile Gly Glu Ser Thr Ile Arg Cys Thr
865                 870                 875                 880

Ser Asp Pro Gln Gly Asn Gly Val Trp Ser Ser Pro Ala Pro Arg Cys
            885                 890                 895
```

-continued

```
Gly Ile Leu Gly His Cys Gln Ala Pro Asp His Phe Leu Phe Ala Lys
            900                 905                 910
Leu Lys Thr Gln Thr Asn Ala Ser Asp Phe Pro Ile Gly Thr Ser Leu
        915                 920                 925
Lys Tyr Glu Cys Arg Pro Glu Tyr Tyr Gly Arg Pro Phe Ser Ile Thr
    930                 935                 940
Cys Leu Asp Asn Leu Val Trp Ser Ser Pro Lys Asp Val Cys Lys Arg
945                 950                 955                 960
Lys Ser Cys Lys Thr Pro Pro Asp Pro Val Asn Gly Met Val His Val
                965                 970                 975
Ile Thr Asp Ile Gln Val Gly Ser Arg Ile Asn Tyr Ser Cys Thr Thr
            980                 985                 990
Gly His Arg Leu Ile Gly His Ser Ser Ala Glu Cys Ile Leu Ser Gly
        995                 1000                1005
Asn Thr Ala His Trp Ser Thr Lys Pro Pro Ile Cys Gln Arg Ile
    1010                1015                1020
Pro Cys Gly Leu Pro Pro Thr Ile Ala Asn Gly Asp Phe Ile Ser
    1025                1030                1035
Thr Asn Arg Glu Asn Phe His Tyr Gly Ser Val Val Thr Tyr Arg
    1040                1045                1050
Cys Asn Leu Gly Ser Arg Gly Arg Lys Val Phe Glu Leu Val Gly
    1055                1060                1065
Glu Pro Ser Ile Tyr Cys Thr Ser Asn Asp Asp Gln Val Gly Ile
    1070                1075                1080
Trp Ser Gly Pro Ala Pro Gln Cys Ile Ile Pro Asn Lys Cys Thr
    1085                1090                1095
Pro Pro Asn Val Glu Asn Gly Ile Leu Val Ser Asp Asn Arg Ser
    1100                1105                1110
Leu Phe Ser Leu Asn Glu Val Val Glu Phe Arg Cys Gln Pro Gly
    1115                1120                1125
Phe Val Met Lys Gly Pro Arg Arg Val Lys Cys Gln Ala Leu Asn
    1130                1135                1140
Lys Trp Glu Pro Glu Leu Pro Ser Cys Ser Arg Val Cys Gln Pro
    1145                1150                1155
Pro Pro Glu Ile Leu His Gly Glu His Thr Pro Ser His Gln Asp
    1160                1165                1170
Asn Phe Ser Pro Gly Gln Glu Val Phe Tyr Ser Cys Glu Pro Gly
    1175                1180                1185
Tyr Asp Leu Arg Gly Ala Ala Ser Leu His Cys Thr Pro Gln Gly
    1190                1195                1200
Asp Trp Ser Pro Glu Ala Pro Arg Cys Ala Val Lys Ser Cys Asp
    1205                1210                1215
Asp Phe Leu Gly Gln Leu Pro His Gly Arg Val Leu Phe Pro Leu
    1220                1225                1230
Asn Leu Gln Leu Gly Ala Lys Val Ser Phe Val Cys Asp Glu Gly
    1235                1240                1245
Phe Arg Leu Lys Gly Ser Ser Val Ser His Cys Val Leu Val Gly
    1250                1255                1260
Met Arg Ser Leu Trp Asn Asn Ser Val Pro Val Cys Glu His Ile
    1265                1270                1275
Phe Cys Pro Asn Pro Pro Ala Ile Leu Asn Gly Arg His Thr Gly
    1280                1285                1290
Thr Pro Ser Gly Asp Ile Pro Tyr Gly Lys Glu Ile Ser Tyr Thr
```

```
            1295                1300                1305
Cys Asp Pro His Pro Asp Arg Gly Met Thr Phe Asn Leu Ile Gly
    1310                1315                1320

Glu Ser Thr Ile Arg Cys Thr Ser Asp Pro His Gly Asn Gly Val
    1325                1330                1335

Trp Ser Ser Pro Ala Pro Arg Cys Glu Leu Ser Val Arg Ala Gly
    1340                1345                1350

His Cys Lys Thr Pro Glu Gln Phe Pro Phe Ala Ser Pro Thr Ile
    1355                1360                1365

Pro Ile Asn Asp Phe Glu Phe Pro Val Gly Thr Ser Leu Asn Tyr
    1370                1375                1380

Glu Cys Arg Pro Gly Tyr Phe Gly Lys Met Phe Ser Ile Ser Cys
    1385                1390                1395

Leu Glu Asn Leu Val Trp Ser Ser Val Glu Asp Asn Cys Arg Arg
    1400                1405                1410

Lys Ser Cys Gly Pro Pro Pro Glu Pro Phe Asn Gly Met Val His
    1415                1420                1425

Ile Asn Thr Asp Thr Gln Phe Gly Ser Thr Val Asn Tyr Ser Cys
    1430                1435                1440

Asn Glu Gly Phe Arg Leu Ile Gly Ser Pro Ser Thr Thr Cys Leu
    1445                1450                1455

Val Ser Gly Asn Asn Val Thr Trp Asp Lys Lys Ala Pro Ile Cys
    1460                1465                1470

Glu Ile Ile Ser Cys Glu Pro Pro Pro Thr Ile Ser Asn Gly Asp
    1475                1480                1485

Phe Tyr Ser Asn Asn Arg Thr Ser Phe His Asn Gly Thr Val Val
    1490                1495                1500

Thr Tyr Gln Cys His Thr Gly Pro Asp Gly Glu Gln Leu Phe Glu
    1505                1510                1515

Leu Val Gly Glu Arg Ser Ile Tyr Cys Thr Ser Lys Asp Asp Gln
    1520                1525                1530

Val Gly Val Trp Ser Ser Pro Pro Pro Arg Cys Ile Ser Thr Asn
    1535                1540                1545

Lys Cys Thr Ala Pro Glu Val Glu Asn Ala Ile Arg Val Pro Gly
    1550                1555                1560

Asn Arg Ser Phe Phe Ser Leu Thr Glu Ile Ile Arg Phe Arg Cys
    1565                1570                1575

Gln Pro Gly Phe Val Met Val Gly Ser His Thr Val Gln Cys Gln
    1580                1585                1590

Thr Asn Gly Arg Trp Gly Pro Lys Leu Pro His Cys Ser Arg Val
    1595                1600                1605

Cys Gln Pro Pro Pro Glu Ile Leu His Gly Glu His Thr Leu Ser
    1610                1615                1620

His Gln Asp Asn Phe Ser Pro Gly Gln Glu Val Phe Tyr Ser Cys
    1625                1630                1635

Glu Pro Ser Tyr Asp Leu Arg Gly Ala Ala Ser Leu His Cys Thr
    1640                1645                1650

Pro Gln Gly Asp Trp Ser Pro Glu Ala Pro Arg Cys Thr Val Lys
    1655                1660                1665

Ser Cys Asp Asp Phe Leu Gly Gln Leu Pro His Gly Arg Val Leu
    1670                1675                1680

Leu Pro Leu Asn Leu Gln Leu Gly Ala Lys Val Ser Phe Val Cys
    1685                1690                1695
```

```
Asp Glu Gly Phe Arg Leu Lys Gly Arg Ser Ala Ser His Cys Val
    1700                1705                1710

Leu Ala Gly Met Lys Ala Leu Trp Asn Ser Ser Val Pro Val Cys
    1715                1720                1725

Glu Gln Ile Phe Cys Pro Asn Pro Pro Ala Ile Leu Asn Gly Arg
    1730                1735                1740

His Thr Gly Thr Pro Phe Gly Asp Ile Pro Tyr Gly Lys Glu Ile
    1745                1750                1755

Ser Tyr Ala Cys Asp Thr His Pro Asp Arg Gly Met Thr Phe Asn
    1760                1765                1770

Leu Ile Gly Glu Ser Ser Ile Arg Cys Thr Ser Asp Pro Gln Gly
    1775                1780                1785

Asn Gly Val Trp Ser Ser Pro Ala Pro Arg Cys Glu Leu Ser Val
    1790                1795                1800

Pro Ala Ala Cys Pro His Pro Pro Lys Ile Gln Asn Gly His Tyr
    1805                1810                1815

Ile Gly Gly His Val Ser Leu Tyr Leu Pro Gly Met Thr Ile Ser
    1820                1825                1830

Tyr Ile Cys Asp Pro Gly Tyr Leu Leu Val Gly Lys Gly Phe Ile
    1835                1840                1845

Phe Cys Thr Asp Gln Gly Ile Trp Ser Gln Leu Asp His Tyr Cys
    1850                1855                1860

Lys Glu Val Asn Cys Ser Phe Pro Leu Phe Met Asn Gly Ile Ser
    1865                1870                1875

Lys Glu Leu Glu Met Lys Lys Val Tyr His Tyr Gly Asp Tyr Val
    1880                1885                1890

Thr Leu Lys Cys Glu Asp Gly Tyr Thr Leu Glu Gly Ser Pro Trp
    1895                1900                1905

Ser Gln Cys Gln Ala Asp Asp Arg Trp Asp Pro Pro Leu Ala Lys
    1910                1915                1920

Cys Thr Ser Arg Ala His Asp Ala
    1925                1930

<210> SEQ ID NO 2
<211> LENGTH: 22
<212> TYPE: DNA
<213> ORGANISM: Artificial Sequence
<220> FEATURE:
<223> OTHER INFORMATION: Beta-actin primer

<400> SEQUENCE: 2
ggaaatcgtg cgtgacatta aa                                              22

<210> SEQ ID NO 3
<211> LENGTH: 17
<212> TYPE: DNA
<213> ORGANISM: Artificial Sequence
<220> FEATURE:
<223> OTHER INFORMATION: Beta-actin primer

<400> SEQUENCE: 3
gcggcagtgg ccatctc                                                    17

<210> SEQ ID NO 4
<211> LENGTH: 24
<212> TYPE: DNA
<213> ORGANISM: Artificial Sequence
<220> FEATURE:
```

<223> OTHER INFORMATION: IL-6 primer

<400> SEQUENCE: 4
ccaacttcca atgctctcct aatg                                    24

<210> SEQ ID NO 5
<211> LENGTH: 24
<212> TYPE: DNA
<213> ORGANISM: Artificial Sequence
<220> FEATURE:
<223> OTHER INFORMATION: IL-6 primer

<400> SEQUENCE: 5
ttcaagtgct ttcaagagtt ggat                                    24

<210> SEQ ID NO 6
<211> LENGTH: 22
<212> TYPE: DNA
<213> ORGANISM: Artificial Sequence
<220> FEATURE:
<223> OTHER INFORMATION: IL-1beta primer

<400> SEQUENCE: 6
cagcaatggt cgggacatag tt                                      22

<210> SEQ ID NO 7
<211> LENGTH: 24
<212> TYPE: DNA
<213> ORGANISM: Artificial Sequence
<220> FEATURE:
<223> OTHER INFORMATION: IL-1beta primer

<400> SEQUENCE: 7
gcattaggaa tagtgcagcc atct                                    24

<210> SEQ ID NO 8
<211> LENGTH: 25
<212> TYPE: DNA
<213> ORGANISM: Artificial Sequence
<220> FEATURE:
<223> OTHER INFORMATION: MCP-1 primer

<400> SEQUENCE: 8
ctttgaatgt gaacttgacc cataa                                   25

<210> SEQ ID NO 9
<211> LENGTH: 23
<212> TYPE: DNA
<213> ORGANISM: Artificial Sequence
<220> FEATURE:
<223> OTHER INFORMATION: MCP-1 primer

<400> SEQUENCE: 9
acagaagtgc ttgaggtggt tgt                                     23

<210> SEQ ID NO 10
<211> LENGTH: 23
<212> TYPE: DNA
<213> ORGANISM: Artificial Sequence
<220> FEATURE:
<223> OTHER INFORMATION: TGF-beta primer

<400> SEQUENCE: 10
acagaagtgc ttgaggtggt tgt                                     23

```
<210> SEQ ID NO 11
<211> LENGTH: 20
<212> TYPE: DNA
<213> ORGANISM: Artificial Sequence
<220> FEATURE:
<223> OTHER INFORMATION: TGF-beta primer

<400> SEQUENCE: 11
cctcgacgtt tgggactgat                                               20

<210> SEQ ID NO 12
<211> LENGTH: 23
<212> TYPE: DNA
<213> ORGANISM: Artificial Sequence
<220> FEATURE:
<223> OTHER INFORMATION: KIM-1 primer

<400> SEQUENCE: 12
agagagagca ggacacaggc ttt                                           23

<210> SEQ ID NO 13
<211> LENGTH: 20
<212> TYPE: DNA
<213> ORGANISM: Artificial Sequence
<220> FEATURE:
<223> OTHER INFORMATION: KIM-1 primer

<400> SEQUENCE: 13
acccgtggta gtcccaaaca                                               20

<210> SEQ ID NO 14
<211> LENGTH: 21
<212> TYPE: DNA
<213> ORGANISM: Artificial Sequence
<220> FEATURE:
<223> OTHER INFORMATION: E-selectin primer

<400> SEQUENCE: 14
gtctgcgatg ctgcctactt g                                             21

<210> SEQ ID NO 15
<211> LENGTH: 22
<212> TYPE: DNA
<213> ORGANISM: Artificial Sequence
<220> FEATURE:
<223> OTHER INFORMATION: E-selectin primer

<400> SEQUENCE: 15
ctgccacaga aagtgccact ac                                            22
```

METHOD OF IMPROVING TRANSPLANT FUNCTION USING SOLUBLE COMPLEMENT RECEPTOR TYPE I (SCR1)

CROSS-REFERENCE TO PRIORITY APPLICATIONS

This application claims priority to U.S. Provisional Application No. 61/407,331 filed Oct. 27, 2010, the contents of which are incorporated herein.

FIELD OF THE INVENTION

The present invention relates to methods and pharmaceutical compositions for inhibiting rejection of transplant organs from brain-dead organ donors, particularly kidney donors. Improvement of transplant function is achieved in the recipient by treatment of donors prior to harvesting the organ intended for transplant. Specifically, the invention relates to the use of pharmaceutical compositions comprising a soluble complement receptor type I (sCR1) to treat brain-dead organ donors, which leads to improvements in organ function after transplant from the donor to a compatible recipient, which in turn enhances transplant survival.

BACKGROUND OF THE INVENTION

Despite an increasing pool of living and non-heart beating donors, most kidneys that are finally transplanted are still derived from heart-beating, brain-dead donors. However, the state of brain death itself is an independent risk factor affecting successful organ transplantation, with grafts from brain-dead donors showing worse renal function and poorer survival rates after transplantation (Terasaki, P I, et al., *N. Engl. J. Med.*, 333(6): 333-6 (1995); Matas, A J, et al., *Transplantation*, 69(1): 54-8 (2000)). In several animal models mimicking brain death and in brain-dead patients, systemic and local organ inflammation has been shown (Nijboer, W N, et al., *Transplantation*, 78(7): 978-86 (2004); Kusaka, M, et al., *Transplantation*, 69(3): 405-10 (2000); Hoeger, S, et al., *Am. J. Transplant.*, 10(3): 477-89 (2010); Schuurs, T A, et al., *Am. J. Transplant.*, 4(12): 1972-81 (2004)).

In previous studies it has been shown that local renal complement is activated in experimental and clinically brain-dead donors (Damman, J, et al., *Transplantation*, 85(7): 923-7 (2008)). Furthermore, it has been shown that systemic complement is activated in deceased human donors, predisposing the kidney graft to a higher risk of acute rejection after transplantation (unpublished data).

The complement system comprises more than 40 different proteins directly or indirectly mediating attack and elimination of microbes, foreign particles and altered self cells via three different pathways of activation: classical pathway, alternative pathway, and lectin pathway (see, *The Complement System*, 2nd revised edition, Rother et al. (eds); Springer Verlag (1998)). The complement system is a major component of innate immunity and is a central host defense against infection. Activation of the complement cascade via the classical pathway, involving antigen-antibody complexes, by the lectin pathway, or by the alternative pathway, involving the recognition of certain cell wall polysaccharides, mediates a range of activities including lysis of microorganisms, chemotaxis, opsonization, stimulation of vascular and other smooth muscle cells, degranulation of mast cells, increased permeability of small blood vessels, directed migration of leukocytes, and activation of B lymphocytes and macrophages. Inherent to complement activation is the generation of the anaphylatoxins C3a and C5a which have chemokinetic and pro-inflammatory properties (Walport, M J, *N. Engl. J. Med.*, 344(14): 1058-66 (2001); Walport, M J, *N. Engl. J. Med.*, 344(15): 1140-4 (2001)).

The membrane attack complex (MAC) is the final product of the activated complement cascade. It is a lytic multi-protein complex that is lethal to pathogens and, at sublytic levels, causes the release of cytokines and growth factors such as beta-FGF and VEGF from nucleated cells (e.g., smooth muscle cells, endothelial cells).

In renal transplantation, the important role of complement activation in the recipient has been extensively shown in models of renal ischemia-reperfusion-injury (IRI). In knock-out models of several complement components, renal IRI could be prevented (Zhou, W, et al. *J. Clin. Invest.*, 105(10): 1363-71 (2000)). Moreover, local expression of complement C3 by the donor kidney negatively affects graft rejection and survival after transplantation (Pratt, J R, et al., *Nat. Med.*, 8(6): 582-7 (2002)). Also post-transplantation, in rejecting grafts, complement is shown to be activated (Serinsoz, E, et al., *Am. J. Transplant.*, 5(6): 1490-4 (2005)).

In the past, several strategies have been used to target renal complement activation in animal models of renal IRI and transplantation. Systemic administration of complement regulatory proteins, monoclonal antibodies against C5 or the C5a receptor (C5aR), or silencing of C3 and C5aR by small interfering RNA (siRNA) have been successful in preventing renal IRI or acute rejection (Arumugam, T V, et al., *Kidney Int.*, 63(1): 134-42 (2003); Gueler, F, et al., *J. Am. Soc. Nephrol.*, 19(12): 2302-12 (2008); Matthijsen, R A, *Transplantation*, 75(3): 375-82 (2003); Pratt, J R, *Transpl. Immunol.*, 4(1): 72-5 (1996); Zheng, X, et al., *Am. J. Transplant.*, 6(9): 2099-108 (2006); Zheng, X, et al., *Am. J. Pathol.*, 173(4): 973-80 (2008).

However, it has not been previously known whether pre-treating an organ donor, in particular a brain-dead organ donor, to target donor systemic and local complement activation would be a viable therapy to improve the function or survival of the organ after transplantation from the donor to a recipient, and a persistent need for new therapeutic approaches to improve transplantation success is evident.

SUMMARY OF THE INVENTION

The present invention relates to the use of a soluble complement receptor type I polypeptide for the therapeutic pre-treatment of brain-dead organ donors to target donor systemic and/or local organ complement activation. In particular aspects, the present invention relates to a method for improving donor organ function in a transplant recipient by pretreatment of the donor, such as a brain-dead organ donor, with a soluble complement receptor type I (sCR1) polypeptide.

The method of the present invention will be particularly useful in the field of kidney transplantation, where the majority of transplant organs are harvested from living but brain-dead donors. Experiments described below in an in vivo renal transplant model have demonstrated that renal function of transplanted kidneys is improved with treatment of the brain-dead donor prior to removal of the kidney from the donor for transplant. Whereas previous studies of complement inhibition have been concerned with treatment of complement activation in the recipient, the present invention relates to an improvement in transplant outcome where circumstances permit treatment of the organ donor prior to excision for transplant of the donor organ.

In one aspect, the present invention provides a new pharmaceutical composition for the treatment of brain-dead organ donors comprising an amount of a soluble CR1 polypeptide effective to inhibit complement and a pharmaceutically acceptable vehicle.

Another aspect of the invention relates to a method for treatment of brain-dead organ donors prior to organ harvest comprising administration of an amount of a soluble CR1 polypeptide effective to inhibit systemic and/or local renal donor complement activation.

In yet another aspect of the invention relates to a method for preparing a transplant organ from a brain-dead organ donor to improve organ function in a recipient of said transplanted organ from said brain-dead organ donor, said method comprising administering to a brain-dead mammalian donor an effective amount to inhibit systemic and/or local complement activation of a soluble complement receptor type I (sCR1) polypeptide prior to excision of said organ from said donor.

Another aspect of the invention relates to a method for improving transplant organ function in a transplant organ recipient comprising: administering to a brain-dead organ donor an amount of a soluble CR1 polypeptide effective to inhibit systemic and/or local organ donor complement activation; removing an organ from said brain-dead organ donor; and transplanting said organ into a recipient.

In yet another aspect of the invention relates to a method of treating transplant organ rejection in a recipient of a transplant from a brain-dead organ donor, said method comprising administering to said brain-dead mammalian donor an effective amount of a soluble complement receptor type I (sCR1) polypeptide.

In one aspect of the invention, the sCR1 polypeptide is selected from the group consisting of a fragment of human CR1 comprising at least short consensus repeats 8-11; a fragment of human CR1 comprising at least short consensus repeats 15-18; a soluble CR1 polypeptide comprising human CR1 short consensus repeats 8-11 and 15-18; a fragment of human CR1 comprising long homologous repeat B; a fragment of human CR1 comprising long homologous repeat C; a fragment of human CR1 comprising long homologous repeats B and C; a fragment of human CR1 comprising long homologous repeats B, C and D; a fragment of human CR1 comprising at least long homologous repeats A and B; a fragment of human CR1 comprising long homologous repeats A, B and C; a fragment of human CR1 comprising long homologous repeats A, B, C and D; a fragment of human CR1 comprising the extracellular domain of CR1; a fragment of human CR1 comprising the extracellular domain of CR1 and having the N-terminal LHR A deleted (sCR1[desLHR-A]); a soluble CR1 polypeptide having modified glycosylation to improve serum half-life in vivo; a soluble CR1 polypeptide having glycosylation modified to exhibit sialyl Lewis X moieties (sCR1-sLe$^x$); a soluble CR1 construct having two or more CR1 polypeptide moieties linked to a carrier molecule; and combinations thereof.

In yet another aspect of the invention, the sCR1 polypeptide is administered by an intradermal, intramuscular, intraperitoneal, intravenous, intra-arterial, subcutaneous, intrathecal, epidural, oral or pulmonary route.

In one aspect of the invention, said organ in the aspects above is selected from the group consisting of liver, kidney, heart, and lung. In one aspect of the invention, said organ is a kidney.

Another aspect of the invention relates to a method for treatment of brain-dead kidney donors prior to organ harvest comprising administration of an amount of a soluble CR1 polypeptide effective to inhibit systemic and/or local renal donor complement activation and to improve renal function of kidney grafts in recipients. In this aspect, administration of the soluble CR1 polypeptide may be intravenous (IV), subcutaneous (SC), intramuscular (IM), intra-arterial, intraperitoneal (IP), intrathecal, pulmonary, or oral.

Pharmaceutical compositions for use in improving renal function of kidney grafts in recipients comprising a soluble complement receptor type I polypeptide and a pharmaceutically acceptable diluent, carrier or excipient are also contemplated. Use of a soluble complement receptor type I polypeptide in the manufacture of a medicament for the treatment of brain-dead organ donors prior to organ harvest to improve organ function of the transplant in the organ recipient is also contemplated.

DETAILED DESCRIPTION

Figure 1:
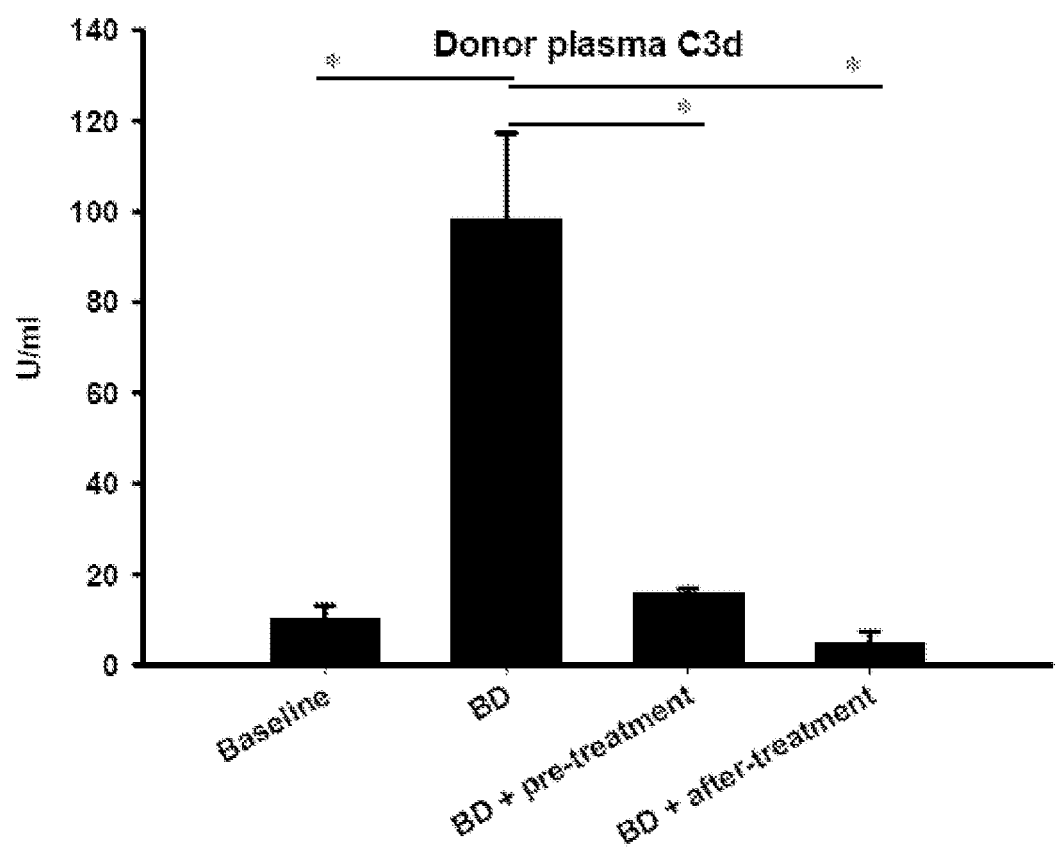
FIG. 1 is a graph showing the levels of plasma C3d in brain-dead Fisher-rat donors and brain-dead donors treated with sCR1. Complement is significantly activated after brain death, as shown by increased levels of C3d in the donors (BD) relative to baseline. Generation of plasma C3d after brain death in the donors is prevented by a single dose of sCR1 (intravenous 25 mg/kg) given 1 hour before (BD+pre-treatment) or after (BD+after-treatment) the induction of brain death. Data is shown as U/ml and expressed as mean values±SEM. Significant differences are indicated (* $P<0.05$).

The present invention is based on the important and surprising discovery that administration of a complement inhibitory protein, in particular soluble CR1, whether prior to or shortly following the onset of brain death, is effective in limiting complement activation in brain-dead organ donors, e.g., brain-dead kidney donors, and improves organ function of the transplant in the recipient (e.g., improves renal function of kidney grafts in kidney transplant recipients).

In order that the invention may be more fully understood, the following terms are defined.

The term "complement inhibitory protein" as used herein refers to any of the complement regulatory proteins that have a negative regulatory activity on complement activation. Complement inhibitory proteins include, specifically, soluble complement receptor type I (sCR1), C4-binding protein (C4-BP), decay accelerating factor (DAF), membrane cofactor protein (MCP), and Factor H.

As used herein, the terms "soluble complement receptor type I", "soluble CR1 polypeptide" or "soluble CR1" or "sCR1" will be used to refer to portions of full-length human complement receptor type I (CR1) protein which, in contrast to the native CR1 proteins, are not expressed on the cell surface as transmembrane proteins but nevertheless exhibit a complement regulatory activity such as C3b binding, C4b binding, the ability to inhibit the classical complement activation pathway and/or the alternative complement activation pathway, and/or the lectin complement activation pathway, etc. In particular, CR1 polypeptides which substantially lack a transmembrane region, or, preferably, which comprise all or part of the extracellular domain of CR1 and retain a complement regulatory activity, are soluble CR1 polypeptides. In a preferred embodiment, the soluble CR1 polypeptides useful in the present invention are secreted by a cell in which they are expressed. Suitable soluble CR1 polypeptides and preparations are described in detail, e.g., in U.S. Pat. No. 5,981,481; U.S. Pat. No. 5,456,909; and U.S. Pat. No. 6,193,979, which are incorporated herein by reference. Soluble CR1 polypeptides having at least one C3b/C4b binding site intact are preferred, as such molecules have the ability to block complement activation via the classical activation pathway and the alternative activation pathway both. Reference to specific complement inhibitory proteins includes fragments of such proteins produced by truncation or splicing-out of unwanted polypeptide segments, so long as complement regulatory activity is retained. Derivatives made by one or more amino acid substitutions or linking to other structures such as carrier proteins or immunoglobulin constant regions are also contemplated, again so long as complement inhibitory activity is retained. In particular, soluble CR1 polypeptides having at least one of the two C3b/C4b binding sites (specifically, short consensus repeats (SCRs) 8-11 and 15-18) intact are preferred, because such molecules will retain the ability to block complement activation via the alternative complement pathway.

Special mention is made of a soluble CR1 polypeptide having glycosylation modified to exhibit sialyl Lewis X moieties (referred to in the scientific literature as "sCR1-sLe'"), as described in U.S. Pat. No. 6,193,979; novel glycoform preparations of soluble CR1 having an increased in vivo half-life as described in U.S. Pat. No. 5,456,909; and soluble constructs having two or more CR1 moieties linked to a carrier molecule, e.g., an sCR1-F(ab)$_2$ fusion, as described in U.S. Pat. No. 6,458,360. Also contemplated are soluble CR1 polypeptides having at least one of the C3b or C4b binding sites intact covalently linked to lipopeptides to facilitate localization on cell surfaces, as disclosed in U.S. Pat. No. 6,713,606. More preferably, the method of the invention utilizes a polypeptide comprising the extracellular domain of mature human CR1 (SEQ ID NO:1).

As used herein, the terms "treatment" or "treating" refers to any regimen that alleviates one or more symptoms of a disorder, e.g., complement-mediated transplant rejection and/or impairment of donor organ function, that inhibits progression of the disorder, that arrests progression or reverses progression (causes regression) of a disorder, or that prevents onset of a disorder. Treatment includes prophylaxis and includes but does not require cure of a disease or disorder.

As used herein, the terms "disorder", "transplant rejection", and "impairment of donor organ function" have the meaning generally known and understood in the art and encompasses any condition that occurs when a transplanted organ or tissue is not accepted by the body of the transplant recipient, including, hyper-acute, acute, and chronic rejection. A diagnosis of a particular disorder by a healthcare professional may be made by direct examination and/or consideration of results of one or more diagnostic tests.

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or "comprises") one or more named elements or steps also describes the corresponding, more limited, composition or method "consisting essentially of" (or "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or "consists of") the named elements or steps to the exclusion of any other unnamed element or step. In any composition or method disclosed herein, known or disclosed equivalents of any named essential element or step may be substituted for that element or step.

The definitions of other terms used herein are those understood and used by persons skilled in the art and/or will be evident to persons skilled in the art from their usage in the text.

The method of this invention can be practiced by using any soluble complement receptor type I polypeptide which is effective to block or limit complement activation. Such complement inhibitory proteins include, for example, soluble complement receptor type I (sCR1) of SEQ ID NO:1, i.e., comprising the extracellular domain of human CR1, or fragments of CR1 that retain complement inhibiting properties, such as the ability to inhibit complement activation, to bind C3b, or to bind both C3b and C4b, or factor I co-factor activity. Preferably, the complement inhibitory protein used in the methods described herein is a soluble (non-membrane-bound) form of human CR1 comprising at least long homologous repeats (LHRs) B and/or C, preferably both LHRs B and C, more preferably long homologous repeats A, B, and C or A, B, C, and D, and most preferably substantially the entire extracellular domain of human CR1 or the molecule sCR1[desLHR-A], which is the extracellular domain of CR1 including the LHRs B, C and D but omitting the N-terminal LHR A (see, Scesney, S. M. et al, Eur. J. Immunol., 26:1729-35 (1996)). Suitable soluble CR1 polypeptides and preparations are described in detail, e.g., in U.S. Pat. Nos. 5,981,481; 5,456,909; and U.S. Pat. No. 6,193,979. Modified sCR1 molecules having, for example, a modified glycosylation, e.g., to improve serum half-life, such as those described in U.S. Pat. No. 5,456,909 may also be used. Soluble CR1 polypeptides having glycosylation modified to exhibit sialyl Lewis X moieties (designated sCR1-sLe$^x$), as described in U.S. Pat. No. 6,193,979, may also be used. And soluble constructs having two or more CR1 moieties linked to a carrier molecule, e.g., an sCR1-F(ab)$_2$ fusion, as described in U.S. Pat. No. 6,458,360, may also be used.

As discussed more fully below, it has been demonstrated herein that administration of sCR1 to a brain-dead prospective organ donor, either prior to the onset of brain death or shortly thereafter, alleviates the effects of undesirable complement activation, and in particular improves organ function of the transplant in organ in recipients after transplant. We have thus discovered that administration of a complement inhibitory protein to a subject in a relevant transplant model reduces and/or ameliorates the pathogenesis of complement activation and terminal complement cascade in prospective brain-dead organ donors. The effects of sCR1 in brain-dead donors has been demonstrated herein in vivo, which demonstrates an important aspect previously unknown, namely, whether sCR1 could be delivered to a prospective brain-dead organ donor, whether the regulatory activity of sCR1 could persist for a meaningful period in vivo to alleviate the effects of brain death complement activation and to improve and/or alleviate the effects of donor complement-mediated transplant rejection and organ function, and whether administration of sCR1 could be effective at a dosage level that would make sCR1 treatment a realistic therapeutic approach to ameliorating allograft rejection and improving survival of transplanted organs in organ recipients.

It has also now been demonstrated that sCR1 can effectively be used to treat brain-dead organ donors prior to organ harvest to inhibit systemic and/or local renal donor complement activation and to improve organ function, e.g., short-term renal function of kidney grafts, in recipients.

The human C3b/C4b receptor, termed complement receptor type I (CR1) or CD35, is naturally present on the membranes of erythrocytes, monocytes/macrophages, granulocytes, B cells, some T cells, splenic follicular dendritic cells, and glomerular podocytes. (Fearon, 1980, *J. Exp. Med.*, 152: 20, Wilson, J. G., et al., 1983, *J. Immunol.*, 131: 684). CR1 specifically binds C3b, C4b, iC3b and iC4b.

CR1 can inhibit the classical and alternative pathway C3/C5 convertases and act as a cofactor for the cleavage of C3b and C4b by factor I, indicating that CR1 also has complement regulatory functions in addition to serving as a receptor. (Fearon, D. T., 1979, *Proc. Natl. Acad. Sci. U.S.A.*, 76: 5867; Lida, K. I. and Nussenzweig, V., 1981, *J. Exp. Med.*, 153: 1138.) In the alternative pathway of complement activation, the bimolecular complex C3bBb is a C3 protease (convertase). CR1 can bind to C3b thereby promoting the dissociation of fragment Bb from the complex. In the alternative pathway of complement activation, the tri-molecular complex C3bC3bBb is a C5 protease (convertase). CR1 can bind to C3bC3b thereby promoting the dissociation of fragment Bb from the complex. Furthermore, binding of C3b to CR1 renders C3b susceptible to irreversible proteolytic inactivation by factor I, resulting in the production of inactivated derivatives of C3b (namely, iC3b, C3d and C3dg). In the classical pathway of complement activation, the bimolecular complex C4bC2a is the C3 convertase. CR1 binds to C4b thereby promoting the dissociation of C2a from the complex. In the classical pathway of complement activation, the complex C3bC4bC2a is the C5 convertase. CR1 binds to C4b and/or C3b thereby promoting the dissociation of C2a from the complex. The binding renders C4b and/or C3b susceptible to irreversible proteolytic inactivation by factor I. Finally, the lectin pathway (also called the mannose binding lectin or MBL pathway) feeds into the classical pathway upstream of the C3 convertase. Thus, CR1 inhibits lectin pathway activation through its inhibitory activities on the classical pathway at the C3 and C5 activation steps.

Several soluble (non-membrane bound) fragments of CR1 have been generated via recombinant DNA procedures by eliminating the transmembrane and cytoplasmic regions from the DNAs being expressed. See, e.g., Fearon et al., Intl. Patent Publn. WO 89/09220, Oct. 5, 1989. The soluble CR1 fragments are functionally active, i.e., retaining the ability to bind C3b and/or C4b, inhibiting complement activation, and demonstrating factor I co-factor activity, depending upon the native CR1 regions the CR1 fragments contain. Such constructs inhibit in vitro the consequences of complement activation such as neutrophil oxidative burst, complement mediated hemolysis, C3a and C5a production, and the production of C5b-9 (MAC). A soluble construct, sCR1/pBSCR1c, also has demonstrated in vivo activity in a reversed passive Arthus reaction (Yeh et al., 1991, *J. Immunol.*, 146:250), suppressed post-ischemic myocardial inflammation and necrosis (Weisman et al., 1990, *Science*, 249: 146-151) and extended survival rates following transplantation (Pruitt et al., 1991, *J. Surg. Res.*, 50: 350; Pruitt et al., 1991, Transplantation, 52: 868).

The complete cDNA coding sequence and amino acid sequence of the human CR1 protein is described in U.S. Pat. No. 5,981,481, which is incorporated herein by reference. The isolation of the full-length CR1 gene, expression and purification of the full-length protein and active fragments thereof, and demonstration of activity in the full-length protein and fragments derived from the full-length protein, are described in U.S. Pat. No. 5,981,481.

The complement inhibitory proteins such as sCR1 that are useful in the methods of the present invention are advantageously produced in quantity using recombinant DNA technology to express the protein in a host cell, such as bacterial cells, mammalian cells, or even plant cells. For the complement inhibitory proteins contemplated herein, mammalian host cells, such as Chinese Hamster ovary (CHO) cells, African Green Monkey kidney (COS) cells, or human cells, retina-derived cells (e.g., PER.C6 cells) being preferred. Yeast expression, *E. coli* expression, baculovirus expression, and plant expression are also contemplated, where non-mammalian glycosylation patterns do not have a significant impact on biological function or pharmacokinetics. Other expression systems for the production of recombinant proteins will also be useful for the production of complement receptor type I polypeptides contemplated herein. The isolated gene encoding the desired protein can be inserted into an appropriate cloning vector. A large number of vector-host systems known in the art may be used. Possible vectors include, but are not limited to, plasmids or modified viruses. The vector system must be compatible with the host cell used. Such vectors include, but are not limited to, bacteriophages such as lambda derivatives, or plasmids such as pBR322, pUC or CDM8 plasmids (Seed, 1987, Nature, 329: 840-842) or derivatives of those well-known vectors. Recombinant molecules can be introduced into host cells via transformation, transfection, infection, electroporation, etc.

Recombinant cells producing a preferred form of sCR1 are deposited with the American Type Culture Collection, Rockville, Md. (accession no. CRL 10052). The deposited cells are a Chinese Hamster ovary cell line DUX B11 carrying plasmid pBSCR1c/pTCSgpt clone 35.6, encoding the extracellular domain of human CR1. Such sCR1 polypeptide in purified form is produced under the product designation TP10 and also by the designation CDX-1135 by Celldex Therapeutics, Inc. (Needham, Mass.).

After expression in a host cell, the soluble CR1 molecules may be isolated and purified by standard methods including chromatography (e.g., ion exchange, affinity, and sizing column chromatography, high pressure liquid chromatography), centrifugation, differential solubility, or by any other standard technique for the purification of proteins. Preferred purification methods are described in U.S. Pat. Nos. 6,316,604, 5,252,216, and 5,840,858, which are incorporated herein by reference.

Soluble CR1 proteins are therapeutically useful in the modulation of complement-mediated diseases, that is, diseases or conditions characterized by inappropriate or undesired complement activation. A soluble CR1 protein or fragment which can bind C3b and/or C4b, retains the ability to inhibit the alternative or classical C3 or C5 convertases, and/or retains factor I cofactor activity, can be used in the methods and uses disclosed herein. In the present invention, we have demonstrated that soluble CR1 can be used to effectively treat brain-dead organ donors prior to organ harvest to inhibit systemic and/or local organ donor complement activation and to improve organ function in the transplant recipient, particularly renal function of kidney grafts in kidney transplant recipients.

In the method of the invention, a soluble CR1 polypeptide is administered to a prospective organ donor, e.g., a recently deceased or brain-dead subject, prior to organ harvest, in order to attenuate complement activation and its role in transplant rejection and organ function. In a brain-dead subject, the circulatory system remains functional, and administered soluble CR1 is distributed to the potential transplant organs by normal blood circulation. In deceased organ donors in which circulation has been lost (e.g., heart death), artificial circulation such as by heart-lung bypass instruments will be needed to deliver soluble CR1 administered to the donor to the organ(s) contemplated for excision and transplant.

In a method of treating a recently deceased or brain-dead prospective organ donor according to the invention, a therapeutically active amount of a soluble complement receptor type I polypeptide is administered to a donor subject prior to organ harvest. The preferred subject is a human. The amount administered should be sufficient to inhibit complement activation. The determination of a therapeutically effective dose is within the capability of practitioners in this art, however, as an example, in embodiments of the method described herein utilizing systemic administration of sCR1 for the treatment of prospective organ donors, an effective human dose will be in the range of 0.1-150 mg/kg; preferably 1-100 mg/kg, more preferably 3-75 mg/kg, most preferably 5-60 mg/kg patient body weight (e.g., 5 mg/kg, 10 mg/kg, 25 mg/kg, 50 mg/kg, etc.). The route of administration may affect the recommended dose. Repeated systemic doses are contemplated in order to maintain an effective level, e.g., to attenuate or inhibit complement activation in a donor's system, depending on the mode of administration adopted.

The treatment of the present invention may be used in connection with harvesting from a brain-dead donor any organ or tissue that might otherwise be damaged by complement activation. Suitable organs benefitting from the method described herein include but are not limited to kidney, lung, heart, liver, skin, heart valves, blood vessels, and the like.

The time of administration of an effective amount of a soluble complement receptor type I polypeptide to a donor will be the earliest possible moment following a determination of brain death, or as soon following brain death as is feasible given legal, ethical, and patient considerations. The attendant physician or transplant surgeon will recognize a multiplicity of factors that influence the timing of organ harvest from a suitable donor and transplant of harvested organs into a suitable recipient(s). Administration of soluble complement receptor type I will be beneficial if administered to a donor at any time between the occurrence of brain death and removal of an organ intended for transplant. Advantageously, administration will occur immediately after brain death occurs or within 5 minutes, within 10 minutes, within 20 minutes, within 40 minutes, within 60 minutes, within 2 hours, within 4 hours, within 8 hours, within 10 hours, within 12 hours, within 16 hours, within 20 hours, within 24 hours, or within 48 hours of brain death being declared, or at any time up to the removal from the brain-dead donor of the organ intended for transplant.

Soluble CR1 may be used in combination or alternating with the administration of other therapeutics prescribed for improving transplant acceptance and organ function, including further treatment of donor and recipient.

For administration, the sCR1 polypeptide may be formulated into an appropriate pharmaceutical composition. Such a composition typically contains as an active ingredient a therapeutically active amount of the sCR1 polypeptide and a pharmaceutically acceptable excipient or carrier such as saline, buffered saline, salt solutions (e.g., BSS®), phosphate buffers, dextrose, or sterile water. Compositions may also comprise specific stabilizing agents such as sugars, including mannose and mannitol.

Various delivery systems are known and can be used for delivery of complement inhibitory proteins such as sCR1 polypeptides in accordance with this invention, e.g., encapsulation in liposomes, microparticles, or microcapsules. Suitable modes of administration include but are not limited to intradermal, intramuscular, intraperitoneal, intravenous, subcutaneous, intrathecal, or epidural injection, and oral or pulmonary delivery.

Pharmaceutical compositions containing one or more complement inhibitory proteins for use in the present invention may be formulated in accordance with routine procedures as a pharmaceutical composition for systemic administration to prospective organ donors. Typically compositions for systemic administration are solutions in sterile aqueous buffer. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by injection, an ampoule of sterile water for injection or saline may be provided so that the ingredients may be mixed prior to administration.

A pharmaceutical pack comprising one or more containers filled with one or more of the ingredients of the pharmaceutical composition is also contemplated.

The following examples illustrate the methods of the present invention. They are provided by way of illustration and not for purposes of limitation.

EXAMPLE 1

In the experiments described herein, statistical analysis was performed using a non-parametric Kruskal-Wallis test with option for multiple comparisons and P<0.05 regarded as significant (StatsDirect 2.2.8, Aswell, UK). Results are presented as mean±SEM (standard error of the mean). For standardized international classification of renal allograft biopsies, that is, BANFF classification (Solez, K, et al., *Kidney Int.*, 44: 411-422 (1993)), Fisher's exact test was applied.

Recombinant soluble complement receptor type I (sCR1) consisting of the extracellular portion of human CR1, produced in CHO cells, was used in the following experiments. The sCR1 was obtained from Celldex Therapeutics, Inc. (Needham, Mass.).

Inbred male Lewis (LEW, RT11) and Fisher (F344, RT11vr) rats weighing 200-250 grams were obtained from Charles River Laboratories (Sulzfeld, Germany). Animals were kept under standard conditions and fed standard rodent chow and water ad libitum. All procedures were performed according to the Guide for the Care and Use of Laboratory Animals published by the National Academy of Sciences and were approved by the local authorities (RP Karlsruhe, A Z 35-9185.81/142/08).

Before induction of brain death, donor animals were anaesthetized with ketamine (Ketanest, Pfizer, Karlsruhe, Germany; 100 mg/kg intraperitoneally) and xylazine (Rompun, BayerVital, Leverkusen, Germany; 6 mg/kg intraperitoneally) and placed on a heating table to keep their body temperature constant. A 3F Fogarty catheter was inserted epidurally in an occipital burr hole and gradually inflated during 1 min with 300 µl of saline. The state of brain death was verified by the occurrence of autonomic storm, the absence of corneal reflexes and by an apnea test. All animals were mechanically ventilated by a tracheostoma with a rodent ventilator (Ugo Basile, Comerio, Italy). Systemic blood pressure MAP (mmHg) was continuously measured (6 h) in the donors using a femoral arterial catheter (Statham pressure transducer P23 Db and a Gould pressure processor; FMI, Ober-Beerbach, Germany). Recipients were anaesthetized with enflurane (Ethrane; Aca Mueller/Adag Pharma, Gottmadingen, Germany). Experiments were performed in the allogeneic Fisher-Lewis rat model. Animals were divided into 3 groups. Donor animals were treated intravenously by microinjection pumps (CMA/100, CMA/Microdialysis, Solna, Sweden) according to the following scheme:

Group 1: Brain death was induced in donor Fisher rats. Brain death lasted 6 hours; the animals were ventilated and treated with NaCl 0.9% (hereinafter the "brain death" group).

Group 2: Fisher donor rats were pre-treated with a single dose of 25 mg/kg sCR1 one hour before brain death induction. Brain death lasted 6 hours and animals were ventilated during the brain death period (hereinafter the "pre-treatment" group).

Group 3: Brain death was induced in donor Fisher rats. One hour after brain death induction animals received a single dose of 25 mg/kg sCR1. Brain death lasted 6 hours and animals were ventilated during the brain death period (hereinafter the "after-treatment" group).

In each group, the left kidney was harvested after 6 hours, flushed with 1 ml of cold UW solution (organ storage solution) and transplanted in allogeneic bilaterally nephrectomised Lewis rats. The transplantation was performed as previously published (Gottmann, U, et al., *Transplantation*, 84(6): 755-62 (2007); Gottmann, U, et al., *Transpl. Int.*, 20(6): 542-9 (2007); Liu, Z, et al., Transplantation, 83(3): 297-303 (2007)). No immunosuppression was administered. Each group consisted of a minimum of six animals. In the donor, blood samples were drawn at baseline and 6 hours after brain death in all three groups. In recipients, blood samples were drawn at days 0, 1, 3, 5 and 7 after transplantation. Blood samples were collected in hirudin tubes to prevent further in vitro complement activation. Samples were stored on ice, centrifuged to obtain plasma, and the plasma samples were stored in aliquots at −80° C. until further analysis. In each assay, fresh frozen plasma samples were used for analysis.

Donor Plasma Complement Activation

To determine whether pre-treatment or after-treatment with sCR1 was able to prevent systemic complement activation in brain-dead donor rats, plasma C3d, known to have a relatively long half-life, was measured.

Complement C3d was quantified by sandwich ELISA. Nunc Maxisorp 96-well plates were coated with monoclonal mouse-anti-rat C3 (Santa Cruz) overnight. After washing, PEG-precipitated samples were incubated in EDTA containing sample buffer for 1 hour at room temperature. After washing, wells were incubated with polyclonal rabbit-anti-human C3d (with cross-reactivity for rat, DAKO), goat-anti-rabbit-peroxidase and TMB as a substrate. Between incubation steps wells were washed with PBS containing 0.05% Tween-20. After the reaction was stopped with 1 M $H_2SO_4$, the amount of reacted substrate was measured at OD 450 nm. A standard curve was made using serial dilutions of a Zymosan activated rat plasma pool. The amount of C3d in measured samples was determined from the standard curve and expressed in units relative to an internal control.

The results of the donor plasma complement activation assay are shown in FIG. 1. As can be seen from FIG. 1, six hours after the inducement of brain death, plasma C3d levels significantly increased compared to baseline levels. In contrast, in both the pre-treatment and after-treatment groups, C3d levels were not elevated after six hours.

Renal Function

Renal function was assessed both in donors and in recipients by plasma creatinine and urea levels. Glomerular filtration rate was estimated by measuring serum creatinine and blood urea nitrogen (BUN), which are accepted measures in both animal studies and in human clinical assessment, with higher levels of serum creatinine and BUN indicating decreasing kidney function. In recipients, plasma creatinine and urea were measured on days 0, 1, 3, 5, and 7 after transplantation, while in donors plasma creatinine was measured at baseline before induction of brain death and at the end of the brain death period.

Figure 2:
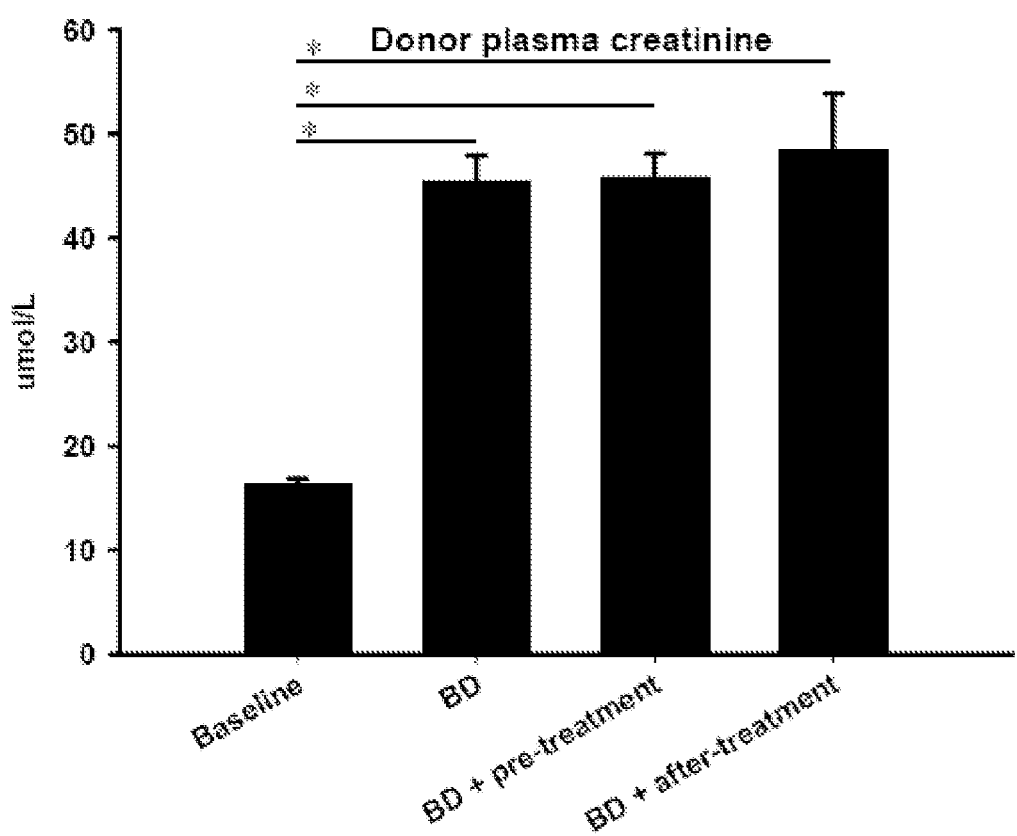
FIG. 2 is a graph showing the levels of plasma creatinine in brain-dead Fisher-rat kidney donors and brain-dead rat kidney donors treated with sCR1. Brain death significantly increased plasma creatinine in the donor rat (BD) relative to baseline, which was not prevented by a single dose of sCR1 (intravenous 25 mg/kg) given 1 hour before (BD+pre-treatment) or after (BD+after-treatment) the induction of brain death. Data is shown as µMol/L and expressed as mean values±SEM.
Figure 3:
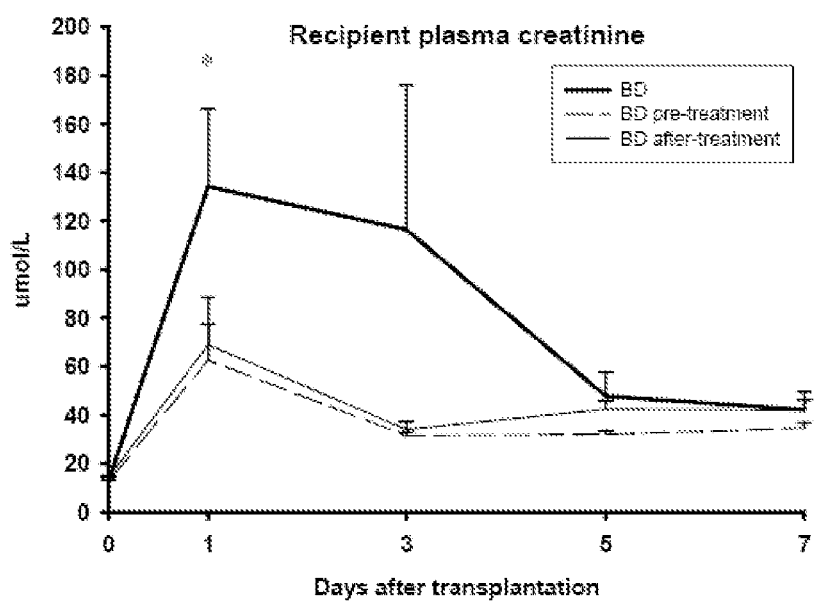
FIG. 3 is a graph showing renal function after transplantation of Lewis rat recipients receiving allogeneic grafts from: 1) brain-dead Fisher rat donors treated with 0.9% saline control (BD), 2) brain-dead donors pre-treated with 25 mg/kg sCR1 at 1 hour prior to induction of brain death (BD pre-treatment), and 3) brain-dead dead donors treated with 25 mg/kg sCR1 at 1 hour after the induction of brain death (BD after-treatment). Plasma creatinine (FIG. 3A) and urea (FIG. 3B) were significantly lower at day 1 after transplantation in recipients receiving grafts from donors treated with sCR1 at 1 hour prior to the induction of brain death compared to recipients of a non-treated donor grafts. Plasma creatinine and urea were similarly lower at day 1 after transplantation in recipients receiving grafts from donors treated with sCR1 at 1 hour after the induction of brain death, although the reductions did not achieve statistical significance in this experiment. Data is shown as mean values±SEM for creatinine (µmol/L) and urea (mg/dL) over time. Significant differences between recipients receiving grafts from sCR1-treated or non-treated donors are indicated (*$P<0.05$).
Figure 3:
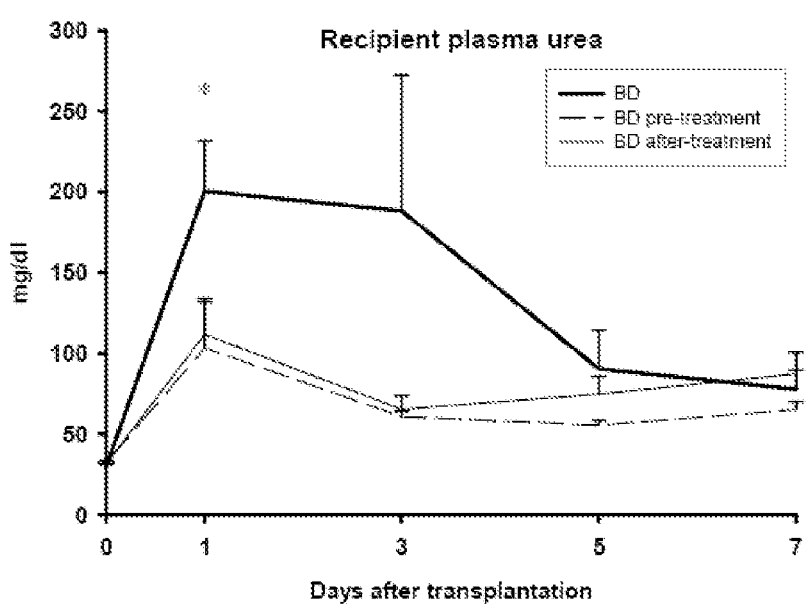

In donors, plasma creatinine significantly increased six hours after brain death, compared to baseline. The increase in plasma creatinine was not prevented in the two sCR1 treatment groups (see, FIG. 2). After transplantation, plasma creatinine and urea were significantly lower at day 1 in recipients of a kidney from sCR1-treated donors compared to recipients of a kidney from an untreated donor. See, FIG. 3.

Renal Inflammation

To assess if inhibition of complement in the donor reduces renal pro-inflammation and induction of pro-fibrosis, Real-Time PCR for IL-6, IL-1beta, MCP-1, TGF-beta and E-selectin was performed.

Total RNA was isolated from whole kidneys by using TRIzol (Life Technologies, Gaithersburg, Md.). RNA samples were verified for absence of genomic DNA contamination by performing RT-PCR reactions in which the addition of reverse transcriptase was omitted, using GAPDH primers. For cDNA synthesis, 1 µl $T_{11}VN$ Oligo-dT (0.5 µg/µl) and 1 µg mRNA were incubated for 10 minutes at 70° C. and cooled directly after that cDNA was synthesized by adding a mixture containing 0.5 µl RnaseOUT® ribonuclease inhibitor (Invitrogen, Carlsbad, USA), 0.5 µl RNase water (Promega), 4 µl 5×first strand buffer (Invitrogen), 2 µl DTT (Invitrogen), 1 µl dNTP's and 1 µl M-MLV reverse transcriptase (Invitrogen, 200U). The mixture was held at 37° C. for 50 minutes. Next, reverse-transcriptase was inactivated by incubating the mixture for 15 minutes at 70° C. Samples were stored at −20° C.

Fragments of several genes were amplified with the primer sets outlined in Table 1.

TABLE 1

Primer sequences used for Real-Time PCR.

| Gene | Primers | Amplicon size (bp) |
|---|---|---|
| β-actin | 5'-GGAAATCGTGCGTGACATTAAA-3' (SEQ ID NO: 2) | 74 |
| | 5'-GCGGCAGTGGCCATCTC-3' (SEQ ID NO: 3) | |
| IL-6 | 5'-CCAACTTCCAATGCTCTCCTAATG-3' (SEQ ID NO: 4) | 89 |
| | 5'-TTCAAGTGCTTTCAAGAGTTGGAT-3' (SEQ ID NO: 5) | |
| IL-1beta | 5'-CAGCAATGGTCGGGACATAGTT-3' (SEQ ID NO: 6) | 75 |
| | 5'-GCATTAGGAATAGTGCAGCCATCT-3' (SEQ ID NO: 7) | |
| MCP-1 | 5'-CTTTGAATGTGAACTTGACCCATAA-3' (SEQ ID NO: 8) | 78 |
| | 5'-ACAGAAGTGCTTGAGGTGGTTGT-3' (SEQ ID NO: 9) | |
| TGF-beta | 5'-GCTCTTGTGACAGCAAAGATAATGTAC-3' (SEQ ID NO: 10) | 66 |
| | 5'-CCTCGACGTTTGGGACTGAT-3' (SEQ ID NO: 11) | |
| KIM-1 | 5'-AGAGAGAGCAGGACACAGGCTTT-3' (SEQ ID NO: 12) | 75 |
| | 5'-ACCCGTGGTAGTCCCAAACA-3' (SEQ ID NO: 13) | |
| E-selectin | 5'-GTCTGCGATGCTGCCTACTTG-3' (SEQ ID NO: 14) | 73 |
| | 5'-CTGCCACAGAAAGTGCCACTAC-3' (SEQ ID NO: 15) | |

Pooled cDNA obtained from brain-dead rats were used as internal references. Gene expression was normalized with the mean of β-actin mRNA content. Real-Time PCR was carried out in reaction volumes of 15 µl containing 10 µl of SYBR Green mastermix (Applied Biosystems, Foster City, USA), 0.4 µl of each primer (50 µM), 4.2 µl of nuclease free water and 10 ng of cDNA. All samples were analysed in triplicate.

Thermal cycling was performed on the Taqman Applied Biosystems 7900HT Real-Time PCR System with a hot start for 2 minutes at 50° C. followed by 10 minutes 95° C. Second stage was started with 15 s at 95° C. (denaturation step) and 60 s at 60° C. (annealing step and DNA synthesis). The latter stage was repeated 40 times. Stage 3 was included to detect formation of primer dimers (melting curve) and begins with 15 s at 95° C. followed by 60 s at 60° C. and 15 s at 95° C.

Primers were designed with Primer Express software (Applied Biosystems) and primer efficiencies were tested by a standard curve for the primer pair resulting from the amplification of serially diluted cDNA samples (10 ng, 5 ng, 2.5 ng, 1.25 ng and 0.625 ng) obtained from brain-dead rats. CR efficiency were found to be $1.8<\epsilon<2.0$. Real-Time PCR products were checked for product specificity on a 1.5% agarose gel. Results were expressed as $2^{-\Delta\Delta CT}$ (CT: Threshold Cycle).

The results are shown in Table 2 below. This experiment was designed to assess if inhibition of complement in the donor reduces renal pro-inflammation and induction of pro-fibrosis. Real-Time PCR for IL-6, IL-1beta, MCP-1, TGF-beta and E-selectin was performed. No significant differences were found between gene expression levels of kidney from sCR1-treated compared to untreated donors before transplantation. As shown in Table 2, however, in renal allografts seven days after transplantation, gene expression levels of inflammatory genes IL-6, IL-1 beta, and TGF-beta were significantly lower in kidneys recovered from sCR1-treated donors.

TABLE 2

Gene expression levels of kidneys at day 7 after transplantation.

| Gene | Group | Relative fold induction |
|---|---|---|
| IL-6 | BD | 2.50 ± 0.86 |
| | BD + pre-treatment | 0.75 ± 0.12 |
| | BD + after-treatment | 0.70 ± 0.12 * |
| IL-1beta | BD | 1.86 ± 1.17 |
| | BD + pre-treatment | 1.21 ± 0.94 * |
| | BD + after-treatment | 1.68 ± 1.31 |
| MCP-1 | BD | 1.26 ± 0.07 |
| | BD + pre-treatment | 1.15 ± 0.07 |
| | BD + after-treatment | 1.21 ± 0.10 |
| TGF-beta | BD | 1.71 ± 0.14 |
| | BD + pre-treatment | 1.40 ± 0.03 |
| | BD + after-treatment | 1.11 ± 0.15 * |
| KIM-1 | BD | 2.01 ± 1.11 |
| | BD + pre-treatment | 0.23 ± 0.03 |
| | BD + after-treatment | 0.58 ± 0.17 |
| E-selectin | BD | 2.41 ± 0.32 |
| | BD + pre-treatment | 1.88 ± 0.44 |
| | BD + after-treatment | 2.05 ± 0.41 |

Data is shown as relative fold induction compared to brain dead (BD) and expressed as mean values ± SEM. Significant differences between gene expression levels of treated kidneys compared to BD kidneys are indicated (* $P < 0.05$).

Histopathology

For BANFF standardized international classification of renal allograft biopsies, Fisher's exact test was applied.

Serial paraffin sections (4 µm) were fixed in 10% neutral buffered formalin for immunohistochemical staining. Histologic grading was performed according to the BANFF 1997 classification. See, K. Solez et al., 2008, *Am. J. Transplantation* 2008, 8:7530760. For BANFF classification, paraffin sections were stained with hematoxylin-eosin, periodic acid-Schiff and trichrome. A minimum of 20 microscopic fields per graft were assessed. Sections were evaluated (under blinding) and graded by a renal pathologist. Histological evaluation and grading included transplant glomerulopathy, tubulointerstitial fibrosis, tubular atrophy, and vasculopathy. The histological scale was from 0 to 3 (0=not present, 1=mild alteration, 2=moderate alteration, and 3=severe alteration).

As shown in Table 3 below, BANFF classification revealed no statistically significant difference in rejection-associated injury at day 7 after transplantation between recipients of a kidney from a sCR1-treated or untreated donor.

TABLE 3

BANFF classification of kidneys 7 days after transplantation.

| BANFF | BD n (%) | BD sCR1 pre-treatment (%) | BD sCR1 after-treatment (%) |
|---|---|---|---|
| I0 | 0 (0) | 0 (0) | 0 (0) |
| I1 | 0 (0) | 0 (0) | 0 (0) |
| I2 | 2 (33.3) | 2 (33.3) | 0 (0) |
| I3 | 4 (66.6) | 4 (66.6) | 6 (100) |
| T0 | 0 (0) | 0 (0) | 0 (0) |
| T1 | 3 (50) | 0 (0) | 0 (0) |
| T2 | 3 (50) | 6 (100) | 6 (100) |
| T3 | 0 (0) | 0 (0) | 0 (0) |
| V0 | 1 (16.7) | 0 (0) | 0 (0) |
| V1 | 5 (83.3) | 6 (100) | 4 (66.6) |
| V2 | 0 (0) | 0 (0) | 0 (0) |
| V3 | 0 (0) | 0 (0) | 2 (33.3) |

Severity of interstitial inflammation (I), tubulitis (T), and intimal arteritis (V) is indicated by the grading scale (0 = not present, 1 = mild alteration, 2 = moderate alteration, and 3 = severe alteration). Numbers in parenthesis represents the % of animals with a given score. No significant difference was observed between the 3 groups.

The unphysiological state of brain death (BD) results in renal inflammation and injury in potential organ donors. We have previously determined significant local and systemic complement activation in both human and rat brain-dead donors. The present study demonstrates that pre-treatment of the brain-dead donor with a complement inhibiting drug, significantly improves renal function after transplantation.

In the experiments described herein, brain-dead donor rats were treated with a single dose of sCR1, a complement inhibiting drug, 1 hour before or 1 hour after brain death induction. Soluble CR1 accelerates the decay of C3 convertases and serves as a cofactor for factor I-mediated degradation of C3b and C4b, thereby inhibiting C3 and C5 convertase formation. Consequently, C3 and C5 will not be activated, and generation of anaphylatoxins and MAC-formation is inhibited (Kinoshita, T., Immunol. Today, 12(9): 291-5 (1991)). Recombinant sCR1 is highly potent in inhibiting complement activation (Weisman, H F, et al., Science, 249(4965): 146-51 (1990)). Given to recipients in a rat allograft model, sCR1 was successfully shown to protect rats against renal allograft injury (Pratt et al., (2002), op. cit.). Following Pratt et al., we used the same dose of 25 mg/kg which totally depresses complement activation shortly after administration with deactivation to 58% after 24 hours. In our brain-dead rat kidney allograft model, systemic complement activation was decreased after 6 hours of brain death to baseline in both the pre- and after-treatment groups. At day 1 after transplantation, grafts from sCR1-treated animals showed a significantly improved renal function compared to grafts derived from untreated animals. Renal function recovered at day 7 after transplantation, at animal sacrifice. Although renal function was already normalized at day 7, lower gene expression levels of inflammatory genes such as IL-6 and IL-1beta were found in kidneys recovered from a treated compared to an untreated donor. It was not possible to prevent rejection associated injury as classified by the BANFF criteria, since no measures to prevent host immunological attack of the renal grafts were taken in this experimental protocol.

The results discussed herein indicate that complement inhibition in the brain-dead donor improves donor organ function in allograft recipients. A single dose of sCR1 given to the donor could not prevent rejection-associated injury in the recipient. However, we emphasize that our study was performed in an allograft model without any immunosuppression to nephrectomised recipients, representing a severe model for acute rejection. Moreover, it is known that complement is also strongly activated in the context of ischemia reperfusion injury and rejection in the recipient, while no sCR1 was given to the recipient in this study. It is therefore contemplated that sCR1, when also given to the recipient, will be of additional value in protecting against rejection associated injury. Pratt et al. showed that local donor C3, instead of C3 produced by the recipient, negatively affects graft survival after transplantation. In an earlier study, we showed that brain death upregulates C3 in both experimental and clinical brain death (Damman, J., (2008) op. cit.). We have now been able to show that brain death leads to upregulation of C3 in the donor kidney. Although sCR1 depleted C3d levels in the blood, renal deposition of C3d and C5b-9 was equal in both treated and untreated animals (data not shown). sCR1 did not prevent local renal complement activation in this model. The kidney itself is a substantial producer of complement components, and possibly sCR1 did not penetrate into the renal interstitium during the time course of this model. Although local renal complement activation occurs, the amplification loop of complement activation will be attenuated since systemic complement is depleted by sCR1. Therefore we observe that inhibition of systemic complement activation in the donor upon brain death, by treatment with sCR1, attenuates renal injury in the donor. Moreover, after transplantation of the allograft, with less brain death-induced tissue injury due to the protective effect of sCR1, the graft is less vulnerable to ischemia reperfusion related injury. Therefore, early graft function in recipients of a kidney from a sCR1-treated donor was found to be better after transplantation.

An important finding of our study is that not only pre-brain death treatment but also after-treatment of the brain-dead donor, in the above examples 1 hour after brain death, improved renal function after transplantation. This is an important finding for clinical applications, since pre-treatment of a donor is of course contrary to ethical considerations and is forbidden by law in many countries. Therefore, from a clinical point of view, it is important to now discover a useful treatment that could be applied to a donor shortly after the diagnosis of brain death which will have a positive effect on the success of an allograft from that donor in its recipient.

The foregoing results show that targeting complement activation in brain-dead donors leads to an improved renal function immediately after renal transplantation. Targeting complement activation in the donor, before or even after the diagnosis of brain death, is a promising approach to improve transplant function of donor organs from brain-dead donors after transplantation.

All publications referred to above are hereby incorporated by reference.

A preferred soluble complement receptor type I polypeptide for use according to the present disclosure has the amino acid sequence:

(SEQ ID NO: 1)

```
Gln Cys Asn Ala Pro Glu Trp Leu Pro Phe Ala Arg Pro Thr Asn Leu
  1               5                  10                  15

Thr Asp Glu Phe Glu Phe Pro Ile Gly Thr Tyr Leu Asn Tyr Glu Cys
              20                  25                  30

Arg Pro Gly Tyr Ser Gly Arg Pro Phe Ser Ile Ile Cys Leu Lys Asn
          35                  40                  45

Ser Val Trp Thr Gly Ala Lys Asp Arg Cys Arg Arg Lys Ser Cys Arg
 50                  55                  60

Asn Pro Pro Asp Pro Val Asn Gly Met Val His Val Ile Lys Gly Ile
 65              70                  75                  80

Gln Phe Gly Ser Gln Ile Lys Tyr Ser Cys Thr Lys Gly Tyr Arg Leu
              85                  90                  95

Ile Gly Ser Ser Ser Ala Thr Cys Ile Ile Ser Gly Asp Thr Val Ile
         100                 105                 110

Trp Asp Asn Glu Thr Pro Ile Cys Asp Arg Ile Pro Cys Gly Leu Pro
         115                 120                 125

Pro Thr Ile Thr Asn Gly Asp Phe Ile Ser Thr Asn Arg Glu Asn Phe
     130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
             165                 170                 175

Asn Asp Asp Gln Val Gly Ile Trp Ser Gly Pro Ala Pro Gln Cys Ile
             180                 185                 190

Ile Pro Asn Lys Cys Thr Pro Pro Asn Val Glu Asn Gly Ile Leu Val
         195                 200                 205

Ser Asp Asn Arg Ser Leu Phe Ser Leu Asn Glu Val Val Glu Phe Arg
 210                 215                 220

Cys Gln Pro Gly Phe Val Met Lys Gly Pro Arg Arg Val Lys Cys Gln
225                 230                 235                 240

Ala Leu Asn Lys Trp Glu Pro Glu Leu Pro Ser Cys Ser Arg Val Cys
             245                 250                 255

Gln Pro Pro Pro Asp Val Leu His Ala Glu Arg Thr Gln Arg Asp Lys
             260                 265                 270

Asp Asn Phe Ser Pro Gly Gln Glu Val Phe Tyr Ser Cys Glu Pro Gly
         275                 280                 285

Tyr Asp Leu Arg Gly Ala Ala Ser Met Arg Cys Thr Pro Gln Gly Asp
     290                 295                 300

Trp Ser Pro Ala Ala Pro Thr Cys Glu Val Lys Ser Cys Asp Asp Phe
305                 310                 315                 320

Met Gly Gln Leu Leu Asn Gly Arg Val Leu Phe Pro Val Asn Leu Gln
             325                 330                 335

Leu Gly Ala Lys Val Asp Phe Val Cys Asp Glu Gly Phe Gln Leu Lys
         340                 345                 350

Gly Ser Ser Ala Ser Tyr Cys Val Leu Ala Gly Met Glu Ser Leu Trp
     355                 360                 365

Asn Ser Ser Val Pro Val Cys Glu Gln Ile Phe Cys Pro Ser Pro Pro
     370                 375                 380

Val Ile Pro Asn Gly Arg His Thr Gly Lys Pro Leu Glu Val Phe Pro
385                 390                 395                 400

Phe Gly Lys Ala Val Asn Tyr Thr Cys Asp Pro His Pro Asp Arg Gly
             405                 410                 415

Thr Ser Phe Asp Leu Ile Gly Glu Ser Thr Ile Arg Cys Thr Ser Asp
         420                 425                 430
```

-continued

Pro Gln Gly Asn Gly Val Trp Ser Ser Pro Ala Pro Arg Cys Gly Ile
        435                 440                 445

Leu Gly His Cys Gln Ala Pro Asp His Phe Leu Phe Ala Lys Leu Lys
    450                 455                 460

Thr Gln Thr Asn Ala Ser Asp Phe Pro Ile Gly Thr Ser Leu Lys Tyr
465                 470                 475                 480

Glu Cys Arg Pro Glu Tyr Tyr Gly Arg Pro Phe Ser Ile Thr Cys Leu
            485                 490                 495

Asp Asn Leu Val Trp Ser Ser Pro Lys Asp Val Cys Lys Arg Lys Ser
                500                 505                 510

Cys Lys Thr Pro Pro Asp Pro Val Asn Gly Met Val His Val Ile Thr
        515                 520                 525

Asp Ile Gln Val Gly Ser Arg Ile Asn Tyr Ser Cys Thr Thr Gly His
    530                 535                 540

Arg Leu Ile Gly His Ser Ser Ala Glu Cys Ile Leu Ser Gly Asn Ala
545                 550                 555                 560

Ala His Trp Ser Thr Lys Pro Pro Ile Cys Gln Arg Ile Pro Cys Gly
            565                 570                 575

Leu Pro Pro Thr Ile Ala Asn Gly Asp Phe Ile Ser Thr Asn Arg Glu
                580                 585                 590

Asn Phe His Tyr Gly Ser Val Val Thr Tyr Arg Cys Asn Pro Gly Ser
        595                 600                 605

Gly Gly Arg Lys Val Phe Glu Leu Val Gly Glu Pro Ser Ile Tyr Cys
    610                 615                 620

Thr Ser Asn Asp Asp Gln Val Gly Ile Trp Ser Gly Pro Ala Pro Gln
625                 630                 635                 640

Cys Ile Ile Pro Asn Lys Cys Thr Pro Pro Asn Val Glu Asn Gly Ile
            645                 650                 655

Leu Val Ser Asp Asn Arg Ser Leu Phe Ser Leu Asn Glu Val Val Glu
                660                 665                 670

Phe Arg Cys Gln Pro Gly Phe Val Met Lys Gly Pro Arg Arg Val Lys
        675                 680                 685

Cys Gln Ala Leu Asn Lys Trp Glu Pro Glu Leu Pro Ser Cys Ser Arg
    690                 695                 700

Val Cys Gln Pro Pro Pro Asp Val Leu His Ala Glu Arg Thr Gln Arg
705                 710                 715                 720

Asp Lys Asp Asn Phe Ser Pro Gly Gln Glu Val Phe Tyr Ser Cys Glu
            725                 730                 735

Pro Gly Tyr Asp Leu Arg Gly Ala Ala Ser Met Arg Cys Thr Pro Gln
                740                 745                 750

Gly Asp Trp Ser Pro Ala Ala Pro Thr Cys Glu Val Lys Ser Cys Asp
        755                 760                 765

Asp Phe Met Gly Gln Leu Leu Asn Gly Arg Val Leu Phe Pro Val Asn
    770                 775                 780

Leu Gln Leu Gly Ala Lys Val Asp Phe Val Cys Asp Glu Gly Phe Gln
785                 790                 795                 800

Leu Lys Gly Ser Ser Ala Ser Tyr Cys Val Leu Ala Gly Met Glu Ser
            805                 810                 815

Leu Trp Asn Ser Ser Val Pro Val Cys Glu Gln Ile Phe Cys Pro Ser
                820                 825                 830

Pro Pro Val Ile Pro Asn Gly Arg His Thr Gly Lys Pro Leu Glu Val
        835                 840                 845

Phe Pro Phe Gly Lys Ala Val Asn Tyr Thr Cys Asp Pro His Pro Asp
    850                 855                 860

```
Arg Gly Thr Ser Phe Asp Leu Ile Gly Glu Ser Thr Ile Arg Cys Thr
865                 870                 875                 880

Ser Asp Pro Gln Gly Asn Gly Val Trp Ser Pro Ala Pro Arg Cys
            885                 890                 895

Gly Ile Leu Gly His Cys Gln Ala Pro Asp His Phe Leu Phe Ala Lys
            900                 905                 910

Leu Lys Thr Gln Thr Asn Ala Ser Asp Phe Pro Ile Gly Thr Ser Leu
        915                 920                 925

Lys Tyr Glu Cys Arg Pro Glu Tyr Tyr Gly Arg Pro Phe Ser Ile Thr
        930                 935                 940

Cys Leu Asp Asn Leu Val Trp Ser Ser Pro Lys Asp Val Cys Lys Arg
945                 950                 955                 960

Lys Ser Cys Lys Thr Pro Pro Asp Pro Val Asn Gly Met Val His Val
            965                 970                 975

Ile Thr Asp Ile Gln Val Gly Ser Arg Ile Asn Tyr Ser Cys Thr Thr
            980                 985                 990

Gly His Arg Leu Ile Gly His Ser Ser Ala Glu Cys Ile Leu Ser Gly
            995                 1000                1005

Asn Thr Ala His Trp Ser Thr Lys Pro Pro Ile Cys Gln Arg Ile
    1010                1015                1020

Pro Cys Gly Leu Pro Pro Thr Ile Ala Asn Gly Asp Phe Ile Ser
    1025                1030                1035

Thr Asn Arg Glu Asn Phe His Tyr Gly Ser Val Val Thr Tyr Arg
    1040                1045                1050

Cys Asn Leu Gly Ser Arg Gly Arg Lys Val Phe Glu Leu Val Gly
    1055                1060                1065

Glu Pro Ser Ile Tyr Cys Thr Ser Asn Asp Asp Gln Val Gly Ile
    1070                1075                1080

Trp Ser Gly Pro Ala Pro Gln Cys Ile Ile Pro Asn Lys Cys Thr
    1085                1090                1095

Pro Pro Asn Val Glu Asn Gly Ile Leu Val Ser Asp Asn Arg Ser
    1100                1105                1110

Leu Phe Ser Leu Asn Glu Val Val Glu Phe Arg Cys Gln Pro Gly
    1115                1120                1125

Phe Val Met Lys Gly Pro Arg Arg Val Lys Cys Gln Ala Leu Asn
    1130                1135                1140

Lys Trp Glu Pro Glu Leu Pro Ser Cys Ser Arg Val Cys Gln Pro
    1145                1150                1155

Pro Pro Glu Ile Leu His Gly Glu His Thr Pro Ser His Gln Asp
    1160                1165                1170

Asn Phe Ser Pro Gly Gln Glu Val Phe Tyr Ser Cys Glu Pro Gly
    1175                1180                1185

Tyr Asp Leu Arg Gly Ala Ala Ser Leu His Cys Thr Pro Gln Gly
    1190                1195                1200

Asp Trp Ser Pro Glu Ala Pro Arg Cys Ala Val Lys Ser Cys Asp
    1205                1210                1215

Asp Phe Leu Gly Gln Leu Pro His Gly Arg Val Leu Phe Pro Leu
    1220                1225                1230

Asn Leu Gln Leu Gly Ala Lys Val Ser Phe Val Cys Asp Glu Gly
    1235                1240                1245

Phe Arg Leu Lys Gly Ser Ser Val Ser His Cys Val Leu Val Gly
    1250                1255                1260

Met Arg Ser Leu Trp Asn Ser Val Pro Val Cys Glu His Ile
    1265                1270                1275
```

-continued

Phe Cys Pro Asn Pro Pro Ala Ile Leu Asn Gly Arg His Thr Gly
            1280                1285                1290

Thr Pro Ser Gly Asp Ile Pro Tyr Gly Lys Glu Ile Ser Tyr Thr
        1295                1300                1305

Cys Asp Pro His Pro Asp Arg Gly Met Thr Phe Asn Leu Ile Gly
    1310                1315                1320

Glu Ser Thr Ile Arg Cys Thr Ser Asp Pro His Gly Asn Gly Val
1325                1330                1335

Trp Ser Ser Pro Ala Pro Arg Cys Glu Leu Ser Val Arg Ala Gly
        1340                1345                1350

His Cys Lys Thr Pro Glu Gln Phe Pro Phe Ala Ser Pro Thr Ile
    1355                1360                1365

Pro Ile Asn Asp Phe Glu Phe Pro Val Gly Thr Ser Leu Asn Tyr
1370                1375                1380

Glu Cys Arg Pro Gly Tyr Phe Gly Lys Met Phe Ser Ile Ser Cys
        1385                1390                1395

Leu Glu Asn Leu Val Trp Ser Ser Val Glu Asp Asn Cys Arg Arg
    1400                1405                1410

Lys Ser Cys Gly Pro Pro Pro Glu Pro Phe Asn Gly Met Val His
1415                1420                1425

Ile Asn Thr Asp Thr Gln Phe Gly Ser Thr Val Asn Tyr Ser Cys
        1430                1435                1440

Asn Glu Gly Phe Arg Leu Ile Gly Ser Pro Ser Thr Thr Cys Leu
    1445                1450                1455

Val Ser Gly Asn Asn Val Thr Trp Asp Lys Lys Ala Pro Ile Cys
1460                1465                1470

Glu Ile Ile Ser Cys Glu Pro Pro Pro Thr Ile Ser Asn Gly Asp
        1475                1480                1485

Phe Tyr Ser Asn Asn Arg Thr Ser Phe His Asn Gly Thr Val Val
    1490                1495                1500

Thr Tyr Gln Cys His Thr Gly Pro Asp Gly Glu Gln Leu Phe Glu
1505                1510                1515

Leu Val Gly Glu Arg Ser Ile Tyr Cys Thr Ser Lys Asp Asp Gln
        1520                1525                1530

Val Gly Val Trp Ser Ser Pro Pro Pro Arg Cys Ile Ser Thr Asn
    1535                1540                1545

Lys Cys Thr Ala Pro Glu Val Glu Asn Ala Ile Arg Val Pro Gly
1550                1555                1560

Asn Arg Ser Phe Phe Ser Leu Thr Glu Ile Ile Arg Phe Arg Cys
        1565                1570                1575

Gln Pro Gly Phe Val Met Val Gly Ser His Thr Val Gln Cys Gln
    1580                1585                1590

Thr Asn Gly Arg Trp Gly Pro Lys Leu Pro His Cys Ser Arg Val
1595                1600                1605

Cys Gln Pro Pro Pro Glu Ile Leu His Gly Glu His Thr Leu Ser
        1610                1615                1620

His Gln Asp Asn Phe Ser Pro Gly Gln Glu Val Phe Tyr Ser Cys
    1625                1630                1635

Glu Pro Ser Tyr Asp Leu Arg Gly Ala Ala Ser Leu His Cys Thr
1640                1645                1650

Pro Gln Gly Asp Trp Ser Pro Glu Ala Pro Arg Cys Thr Val Lys
        1655                1660                1665

Ser Cys Asp Asp Phe Leu Gly Gln Leu Pro His Gly Arg Val Leu
    1670                1675                1680

-continued

```
Leu Pro Leu Asn Leu Gln Leu Gly Ala Lys Val Ser Phe Val Cys
    1685                1690                1695

Asp Glu Gly Phe Arg Leu Lys Gly Arg Ser Ala Ser His Cys Val
    1700                1705                1710

Leu Ala Gly Met Lys Ala Leu Trp Asn Ser Ser Val Pro Val Cys
    1715                1720                1725

Glu Gln Ile Phe Cys Pro Asn Pro Pro Ala Ile Leu Asn Gly Arg
    1730                1735                1740

His Thr Gly Thr Pro Phe Gly Asp Ile Pro Tyr Gly Lys Glu Ile
    1745                1750                1755

Ser Tyr Ala Cys Asp Thr His Pro Asp Arg Gly Met Thr Phe Asn
    1760                1765                1770

Leu Ile Gly Glu Ser Ser Ile Arg Cys Thr Ser Asp Pro Gln Gly
    1775                1780                1785

Asn Gly Val Trp Ser Ser Pro Ala Pro Arg Cys Glu Leu Ser Val
    1790                1795                1800

Pro Ala Ala Cys Pro His Pro Pro Lys Ile Gln Asn Gly His Tyr
    1805                1810                1815

Ile Gly Gly His Val Ser Leu Tyr Leu Pro Gly Met Thr Ile Ser
    1820                1825                1830

Tyr Ile Cys Asp Pro Gly Tyr Leu Leu Val Gly Lys Gly Phe Ile
    1835                1840                1845

Phe Cys Thr Asp Gln Gly Ile Trp Ser Gln Leu Asp His Tyr Cys
    1850                1855                1860

Lys Glu Val Asn Cys Ser Phe Pro Leu Phe Met Asn Gly Ile Ser
    1865                1870                1875

Lys Glu Leu Glu Met Lys Lys Val Tyr His Tyr Gly Asp Tyr Val
    1880                1885                1890

Thr Leu Lys Cys Glu Asp Gly Tyr Thr Leu Glu Gly Ser Pro Trp
    1895                1900                1905

Ser Gln Cys Gln Ala Asp Asp Arg Trp Asp Pro Pro Leu Ala Lys
    1910                1915                1920

Cys Thr Ser Arg Ala His Asp Ala
    1925                1930
```

---

What is claimed is:

1. A method for preparing a transplant organ from a brain-dead organ donor to improve organ function in a recipient of said transplanted organ from said brain-dead organ donor, said method comprising administering to a brain-dead mammalian donor an effective amount to inhibit systemic and/or local complement activation of a soluble complement receptor type I (sCR1) polypeptide prior to excision of said organ from said donor.

2. A method for improving transplant organ function in a transplant organ recipient comprising:
   administering to a brain-dead organ donor an amount of a soluble CR1 polypeptide effective to inhibit systemic and/or local organ donor complement activation;
   removing an organ from said brain-dead organ donor; and
   transplanting said organ into a recipient.

3. A method of treating transplant organ rejection in a recipient of a transplant from a brain-dead organ donor, said method comprising administering to said brain-dead mammalian donor an effective amount of a soluble complement receptor type I (sCR1) polypeptide.

4. The method according to any of claims 1-3, wherein said sCR1 polypeptide is selected from the group consisting of a fragment of human CR1 comprising at least short consensus repeats 8-11;
   a fragment of human CR1 comprising at least short consensus repeats 15-18;
   a soluble CR1 polypeptide comprising human CR1 short consensus repeats 8-11 and 15-18;
   a fragment of human CR1 comprising long homologous repeat B;
   a fragment of human CR1 comprising long homologous repeat C;

a fragment of human CR1 comprising long homologous repeats B and C;
a fragment of human CR1 comprising long homologous repeats B, C and D;
a fragment of human CR1 comprising at least long homologous repeats A and B;
a fragment of human CR1 comprising long homologous repeats A, B and C;
a fragment of human CR1 comprising long homologous repeats A, B, C and D;
a fragment of human CR1 comprising the extracellular domain of CR1;
a fragment of human CR1 comprising the extracellular domain of CR1 and having the N-terminal LHR A deleted (sCR1 [desLHR-A]);
a soluble CR1 polypeptide having modified glycosylation to improve serum half-life in vivo;
a soluble CR1 polypeptide having glycosylation modified to exhibit sialyl Lewis X moieties (sCR1-sLe$^x$);
a soluble CR1 construct having two or more CR1 polypeptide moieties linked to a carrier molecule; and
combinations thereof.

5. The method according to claim 4, wherein said sCR1 polypeptide is administered by an intradermal, intramuscular, intraperitoneal, intravenous, intra-arterial, subcutaneous, intrathecal, epidural, oral or pulmonary route.

6. The method according to claim 5, wherein said organ is selected from the group consisting of liver, kidney, heart, and lung.

7. The method according to claim 6, wherein said organ is a kidney.

* * * * *